(12) United States Patent
Collins et al.

(10) Patent No.: US 11,166,833 B2
(45) Date of Patent: Nov. 9, 2021

(54) LINE PULL ASSEMBLY FOR A PROSTHETIC DELIVERY DEVICE

(71) Applicant: Cook Medical Technologies LLC, Bloomington, IN (US)

(72) Inventors: James Collins, Red Hill (AU); Logan Smith, Mount Gravatt (AU)

(73) Assignee: Cook Medical Technologies LLC, Bloomington, IN (US)

( * ) Notice: Subject to any disclaimer, the term of this patent is extended or adjusted under 35 U.S.C. 154(b) by 42 days.

(21) Appl. No.: 16/398,514

(22) Filed: Apr. 30, 2019

(65) Prior Publication Data

US 2020/0345524 A1 Nov. 5, 2020

(30) Foreign Application Priority Data

Apr. 30, 2019 (AU) ................................ 2019203004

(51) Int. Cl.
*A61F 2/95* (2013.01)
*A61M 25/01* (2006.01)
*A61M 25/09* (2006.01)

(52) U.S. Cl.
CPC ............ *A61F 2/95* (2013.01); *A61M 25/0147* (2013.01); *A61F 2/9517* (2020.05); *A61M 25/09041* (2013.01)

(58) Field of Classification Search
CPC .......... A61F 2/9517; A61F 2/966; A61F 2/95; A61F 2/954; A61F 2/962; A61F 2002/9511; A61F 2002/9534; A61M 2025/0175; A61M 2025/0681; A61M 25/09041;

(Continued)

(56) References Cited

U.S. PATENT DOCUMENTS 6,471,722 B1 10/2002 Inoue
6,878,161 B2 4/2005 Lenker
7,435,253 B1 10/2008 Hartley et al.
(Continued)

FOREIGN PATENT DOCUMENTS

AU 2012258395 7/2013
CN 105943212 A 9/2016
(Continued)

OTHER PUBLICATIONS

European Search Report for EP Application No. 18275158.6, dated May 15, 2019, 8 pages.

*Primary Examiner* — Tan-Uyen T Ho
*Assistant Examiner* — Bridget E. Rabaglia
(74) *Attorney, Agent, or Firm* — Crowell & Moring LLP

(57) ABSTRACT

A line pull assembly for a prosthetic delivery device includes a rail assembly defining a rail cavity, a longitudinal axis and a hand-gripable slider assembly. The slider is mounted to the rail assembly for sliding movement along it. The slider has a body slidably mounted to the rail assembly, the body having an inner body portion within the rail cavity. A line receiver for receiving a pullable line sits within the inner body portion. A release ring is mounted around the rail assembly and is operably connected to the inner body portion. The slider is locked against sliding movement until the release ring is moved the unlocked position. In the unlocked position, the inner body portion is slideably moveable by sliding movement of the release ring to transfer a pulling force through the line receiver.

20 Claims, 17 Drawing Sheets

(58) Field of Classification Search
CPC .......... A61M 25/0147; A61M 25/0905; A61B 2017/2924
See application file for complete search history.

(56) References Cited

U.S. PATENT DOCUMENTS

| | | | |
|---|---|---|---|
| 8,852,266 B2 | 10/2014 | Brooks et al. | |
| 9,095,683 B2 | 8/2015 | Hall et al. | |
| 9,220,619 B2 | 12/2015 | Ramos et al. | |
| 9,370,421 B2 | 6/2016 | Crisostomo et al. | |
| 9,486,350 B2 | 11/2016 | Argentine | |
| 9,504,555 B2 | 11/2016 | Hartley et al. | |
| 9,849,016 B2 | 12/2017 | Beard et al. | |
| 2003/0187469 A1* | 10/2003 | Olson | A61F 11/006 606/162 |
| 2006/0129181 A1 | 6/2006 | Callol et al. | |
| 2007/0299499 A1 | 12/2007 | Hartley | |
| 2009/0099650 A1 | 4/2009 | Bolduc | |
| 2011/0077731 A1 | 3/2011 | Lee et al. | |
| 2011/0307048 A1 | 12/2011 | Ivancev | |
| 2014/0052232 A1 | 2/2014 | Cragg et al. | |
| 2014/0121750 A1* | 5/2014 | Hadley | A61F 2/07 623/1.11 |
| 2015/0230955 A1* | 8/2015 | Farag Eells | A61F 2/95 623/1.11 |
| 2015/0335452 A1* | 11/2015 | Rao | A61F 2/95 623/23.66 |
| 2016/0338864 A1* | 11/2016 | Vad | A61F 2/9661 |
| 2018/0178007 A1* | 6/2018 | Shuros | A61N 1/0573 |
| 2019/0167456 A1 | 6/2019 | Collins et al. | |

FOREIGN PATENT DOCUMENTS

| | | | |
|---|---|---|---|
| WO | WO 2008/042270 A1 | 4/2008 | |
| WO | WO 2011/159504 A1 | 12/2011 | |

\* cited by examiner

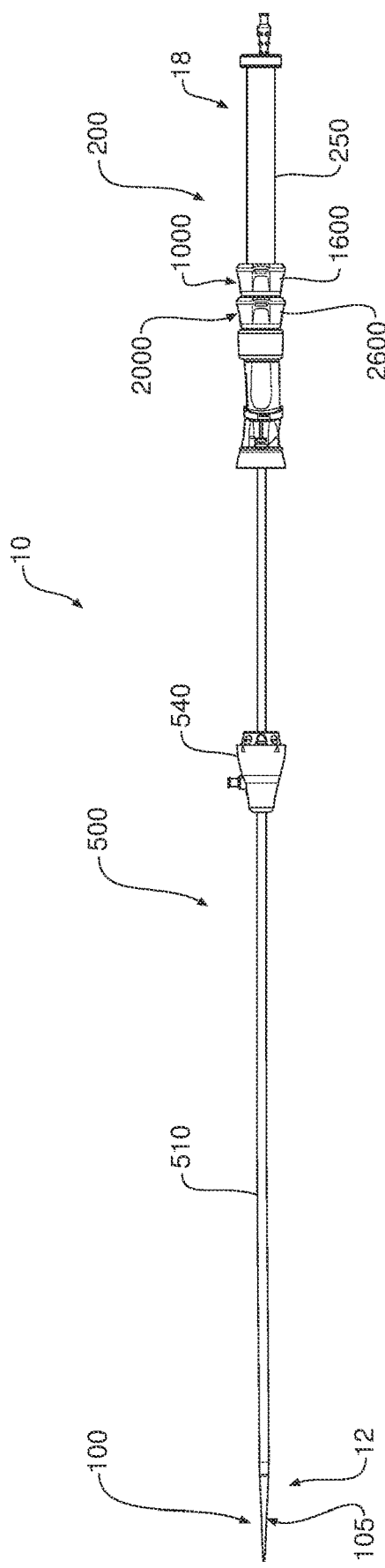
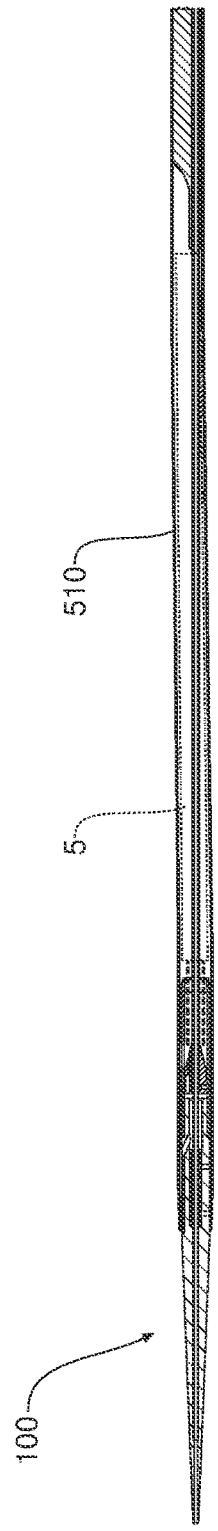
Figure 1A
Figure 1B

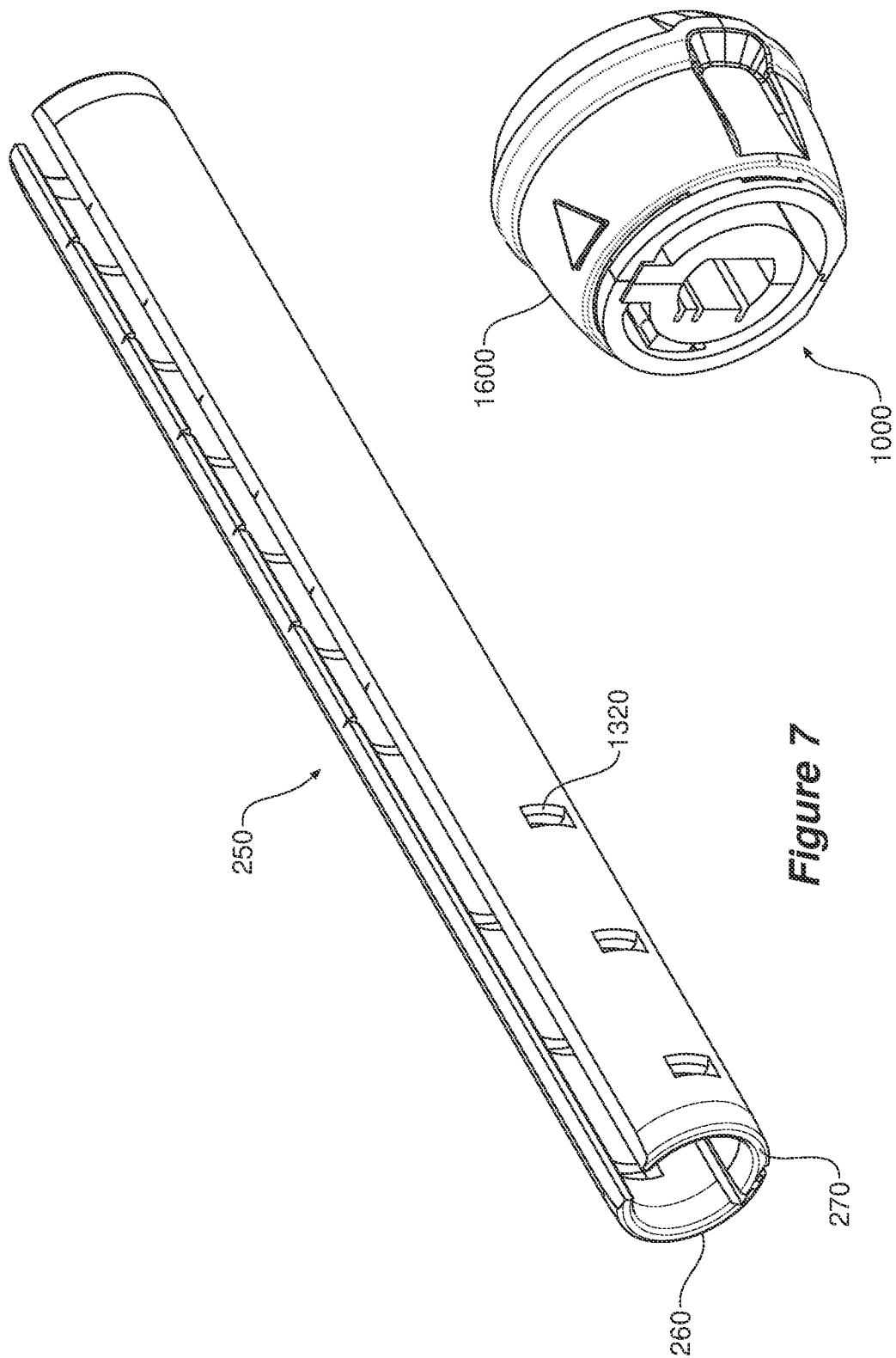

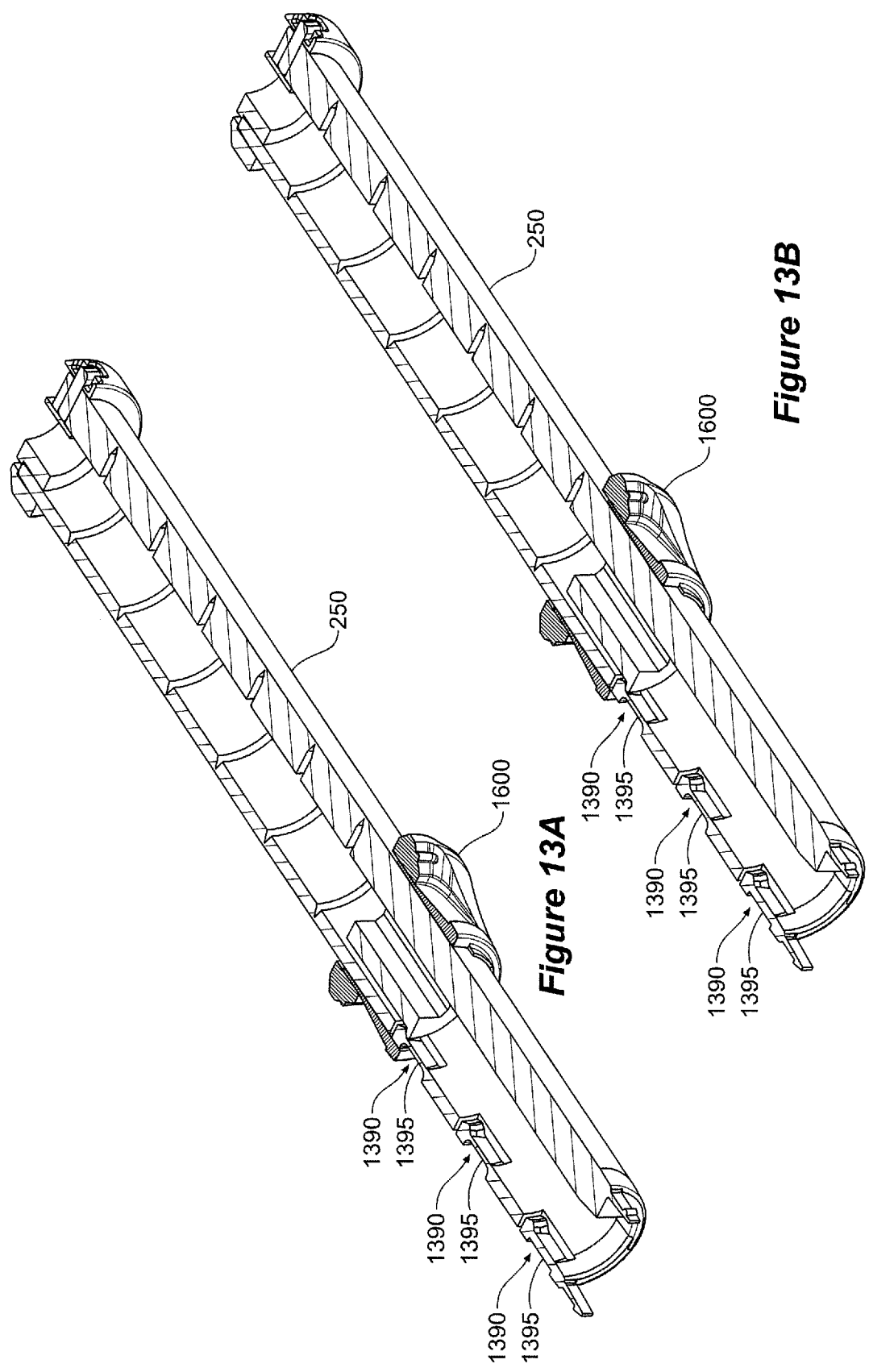

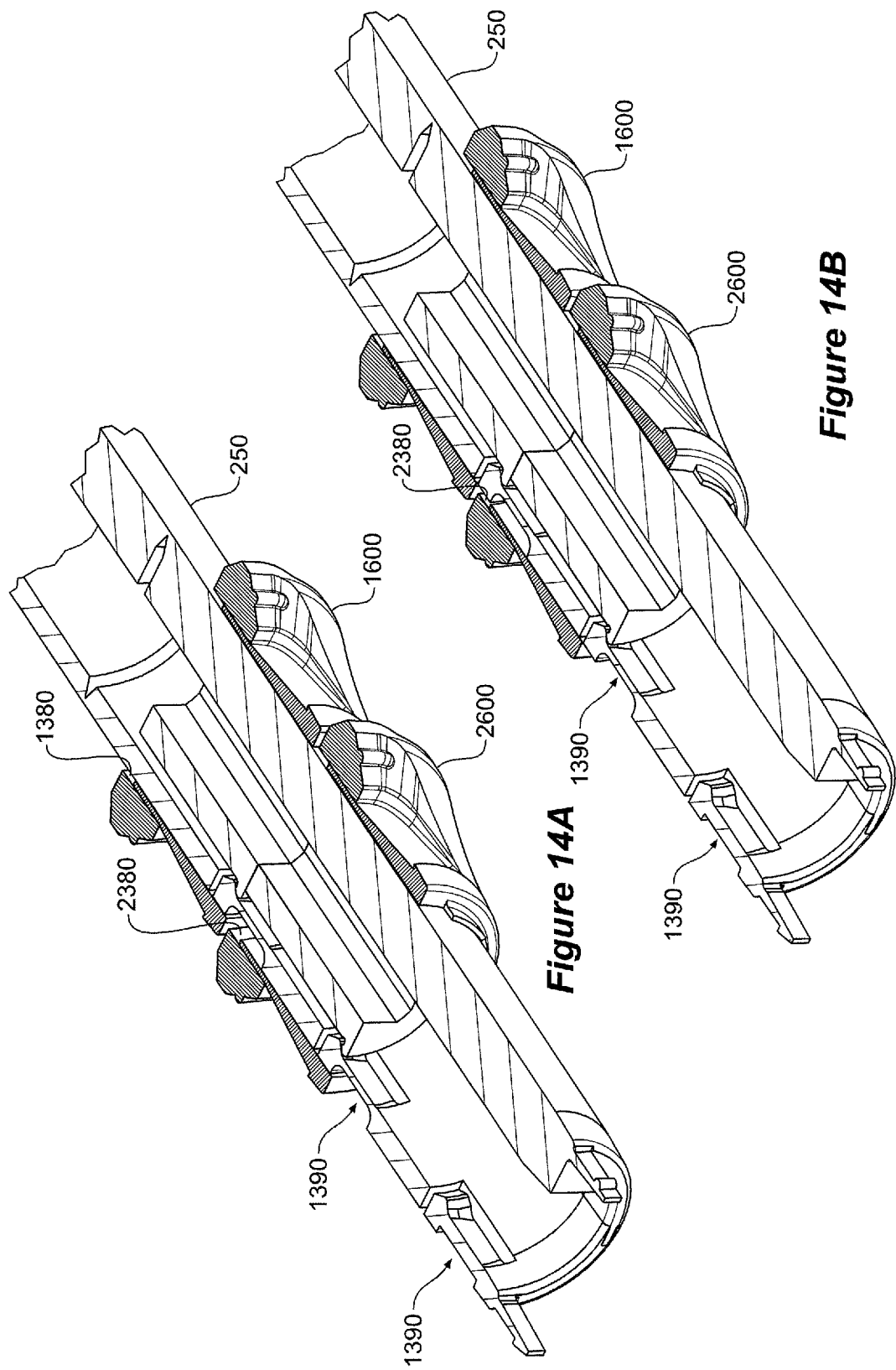

LINE PULL ASSEMBLY FOR A PROSTHETIC DELIVERY DEVICE

CROSS REFERENCE TO RELATED APPLICATIONS

This application claims the benefit of Australian patent application No. 2019203004 filed on Apr. 30, 2019 entitled "A LINE PULL ASSEMBLY FOR A PROSTHETIC DELIVERY DEVICE" the entire contents of which are incorporated herein by reference.

TECHNICAL FIELD

The present invention relates to endografts and their delivery systems, sometimes referred to as endoluminal delivery device assemblies. In particular, the present invention relates to endoluminal delivery device assemblies capable of delivering prostheses, endografts or stent grafts into the vascular system of humans or animals.

BACKGROUND OF THE INVENTION

Stent graft and delivery devices are used in aortic intervention. They are used by vascular surgeons to treat aneurysms and to repair regions of the aorta, including the aortic arch, the thoracic aorta, the abdominal aorta and the aortic bifurcation.

Delivery devices allow deployment of intraluminal prostheses or endografts into the lumen of a patient from a remote location.

Numerous devises and procedures have been developed that involve the percutaneous insertion of a prosthesis into a body lumen, such as a blood vessel or duct, of a patient's body. Such a prosthesis may be introduced into the lumen by a variety of known techniques. For example, a wire guide may be introduced into a blood vessel using the Seldinger technique. This technique involves creating a surgical opening in the vessel with a needle and inserting a wire guide into the vessel through a bore of the needle. The needle can be withdrawn, leaving the wire guide in place. A delivery device is then inserted over the wire guide and into the vessel. The delivery device may be used in conventional fashion to insert into the blood vessel a variety of prostheses, such as stents, stent grafts, catheters, cardiac leads, balloons, and the like.

For example, the delivery device may be used to deliver and deploy an expandable prosthesis, such as a stent graft, to an aneurysmal blood vessel site. A stent graft is usually formed from a tubular body of a biocompatible graft material with one or more stents mounted into or onto the tubular body to provide support therefor. The stents may be balloon expandable stents and/or self-expanding stents. The deployment of the prosthesis into the lumen of a patient from a remote location by the use of an introducer delivery and deployment device is described in, for example, U.S. Pat. No. 7,435,253 to Hartley entitled "A Prosthesis and a Method and Means of Deploying a Prosthesis", which is incorporated herein by reference in its entirety.

Delivery devices are configured to retain prostheses in a delivery configuration during delivery to the desired deployment site. The delivery catheter typically includes an inner catheter/cannula spaced from an outer sheath to define a prosthesis retaining region for receiving the prosthesis. The prosthesis is loaded onto an inner cannula along a prosthesis retaining region, with an outer sheath retaining the prosthesis in the delivery configuration. After the delivery device is delivered to the desired deployment site, the prosthesis may be deployed, for example, with retraction of the outer sheath relative to the inner cannula away from the prosthesis to allow for expansion thereof. Accurate placement of an appropriately sized prosthesis generally sufficiently covers the target site for treatment and the ends of the prosthesis are typically engaged with healthy tissue of the body lumen.

Endovascular delivery devices require significant expertise and experience to operate. Ease of operation and correct sequencing of various manual operations performed outside the body (at a distal end of a delivery device) are required for successful and optimum deployment of an endograft. It is desirable to make operation as intuitive and foolproof as possible.

Endovascular delivery devices should, where ever possible, avoid catch points and should be robust against misuse or damage.

It is an object of the invention to provide an improved endograft and delivery device assembly.

Throughout this specification, the term "distal" with respect to a portion of the aorta, a deployment device or an endograft means the end of the aorta, deployment device or endograft further away in the direction of blood flow from the heart and the term "proximal" means the portion of the aorta deployment device or end of the endograft nearer to the heart in the direction of blood flow.

SUMMARY OF THE INVENTION

According to an aspect of the invention, a line pull assembly for a prosthetic delivery device comprises:
  a rail assembly defining an internal rail cavity and having a longitudinal axis; and
  a first hand-gripable slider assembly, the first slider assembly mounted to the rail assembly for relative sliding movement with respect to the rail assembly along the longitudinal axis, the first slider assembly comprising:
  a slidably mounted to the rail assembly, the body having an inner body portion within the rail cavity, the inner body portion comprising a line receiver for receiving a pullable line; and
  a release ring mounted around the rail assembly and operably connected to the inner body portion, the release ring slideably moveable with respect to the inner body portion along the longitudinal axis from a locked position to an unlocked position,
  wherein, the first slider assembly is locked against sliding movement with respect to the rail assembly until the release ring is moved the unlocked position and,
  wherein, in the unlocked position, the inner body portion is slideably moveable by sliding movement of the release ring to transfer a pulling force through the line receiver.

In one form the release ring comprises a hand-gripable external annular surface extending 360 degrees around an outer body portion of the body,
  whereby the release ring is hand-actuatable irrespective of its orientation about the longitudinal axis.

In one form the assembly further comprises a first detent pair between the body and the release ring, the first detent pair arranged and constructed to hold the release ring in the locked position.

In one form the assembly further comprises a second detent pair between the body and the release ring, the second detent pair arranged and constructed to hold the release ring in the unlocked position.

In one form the assembly the first detent pair comprises a first detent projection and a first detent recess and the second detent pair comprises a second detent projection and a second detent recess.

In one form the assembly further comprises a locking assembly, the locking assembly comprising a pair of co-operating surfaces including a first surface and a second surface, wherein the first surface of the pair of co-operating surfaces is radially movable with respect to the longitudinal axis in the unlocked positon so as to allow relative movement between the first surface and the second surface, and wherein, in the locked position, the first and second surfaces are engaged in the locked position so as to limit relative axial movement.

In one form the first surface is on a flexible arm connected to either one of the first slider assembly and the rail assembly and the second surface is on the other of the first slider assembly and the rail assembly.

In one form at least one of the first and second surfaces of the pair of co-operating surfaces is radially moveable with respect to the other of the first and second surfaces so as to allow disengagement when the release ring is in the unlocked position.

In one form the lock further comprises a third surface, the third surface on the flexible arm and facing radially outward with respect to the longitudinal axis.

In one form the lock further comprises a proximal blocking face on the release ring and wherein, in the locked position, the third surface is blocked from radially outward movement by the proximal blocking face on the release ring, thereby limiting radial movement of at least one of the first and second surfaces with respect to the other of the first and second surfaces of the pair of co-operating surfaces.

In one form the flexible arm is attached to, or forms part of, the body and includes a necked portion.

In an alternative form the flexible arm is attached to, or forms part of, the rail assembly.

In one form the assembly further comprises a second hand-gripable slider assembly, the second slider assembly mounted on the rail assembly adjacent to the first slider assembly such that relative sliding movement of the second slider assembly with respect to the rail assembly is blocked by the first hand-gripable slider assembly in an initial configuration, such that the second hand-gripable slider assembly is only slidable with respect to the rail assembly after the first hand-gripable slider assembly has been slid away from the second hand-gripable slider assembly.

In one form the assembly further comprises the second hand-gripable slider assembly comprises a distal blocking face, the distal blocking face arranged and constructed to prevent the release ring of the first hand grippable slider assembly slideably moving with respect to the inner body portion from the locked position to the unlocked position before the first hand-gripable slider assembly has been slid away from the second hand-gripable slider assembly.

According to another aspect of the invention, an endovascular delivery device, for delivering an endograft, comprises:
 a handle assembly at a distal end thereof;
 a nose assembly 105 at a proximal end thereof,
 a guide wire catheter 40 extending through the handle assembly, the guide wire catheter 40 being affixed at a proximal end thereof to nose assembly 105;
 an endograft receiving portion extending distally with respect to the nose assembly 105;
 a pullable line extending from the handle to the endograft receiving portion; and
 a line pull assembly, the assembly comprising:
  a rail assembly within the handle assembly defining an internal rail cavity and having a longitudinal axis; and
  a first hand-gripable slider assembly, the first slider assembly mounted to the rail assembly for relative sliding movement with respect to the rail assembly along the longitudinal axis, the first slider assembly comprising:
   a body slidably mounted to the rail assembly, the body having an inner body portion within the rail cavity, the inner body portion comprising a line receiver connected to the pullable line; and
   a release ring mounted around the rail assembly and operably connected to the inner body portion, the release ring slideably moveable with respect to the inner body portion along the longitudinal axis from a locked position to an unlocked position,
  wherein, the first slider assembly is locked against sliding movement with respect to the rail assembly until the release ring is moved the unlocked position and,
  wherein, in the unlocked position, the inner body portion is slideably moveable by sliding movement of the release ring to transfer a pulling force to the pullable line.

In one form the release ring comprises a hand-gripable external annular surface extending 360 degrees around the outer body portion,
 whereby the release ring is hand-actuatable irrespective of its orientation about the longitudinal axis.

In one form the endovascular delivery device the pullable line is a wire.

In one form the endovascular delivery device the pullable line comprises a reducing trigger wire having a proximal end for releasing diameter reducing ties in the endograft.

In one form the endovascular delivery device further comprises a first detent pair between the body and the release ring, the first detent pair arranged and constructed to hold the release ring in the locked position.

According to yet another aspect of the invention, an endovascular delivery device, for delivering an endograft, comprises:
 a handle assembly at a distal end thereof;
 a nose assembly 105 at a proximal end thereof,
 a guide wire catheter 40 extending through the handle assembly, the guide wire catheter 40 being affixed at a proximal end thereof to nose assembly 105;
 an endograft receiving portion extending distally with respect to the nose assembly 105;
 a pullable wire extending from the handle to the endograft receiving portion; and
 a wire pull assembly, the assembly comprising:
  a rail assembly within the handle assembly defining an internal rail cavity and having a longitudinal axis; and
  a first hand-gripable slider assembly, the first slider assembly mounted to the rail assembly for relative sliding movement with respect to the rail assembly along the longitudinal axis, the first slider assembly comprising:
   a body slidably mounted to the rail assembly, the body having an inner body portion within the rail cavity, the inner body portion comprising a wire receiver connected to the pullable wire; and
  a release ring comprising a hand-gripable external annular surface extending 360 degrees around the outer body portion, the release ring mounted around the rail assembly and operably connected to the inner body portion, the release ring slideably moveable with respect to the inner body portion along the longitudinal axis from a locked position to an unlocked position, wherein, the first slider assembly is locked against sliding movement with respect to the rail assembly until the release ring is moved the unlocked position and, wherein, in the unlocked position, the inner body portion is slideably moveable by sliding movement of the release ring to transfer a pulling force to the pullable wire.

BRIEF DESCRIPTION OF THE DRAWING

Embodiments of the present invention will be discussed with reference to the accompanying drawings wherein:

FIG. 1A shows an endovascular delivery device according to the invention in a side view;

FIG. 1B shows a proximal end of the device of FIG. 1A;

FIG. 7 is an isometric view of a rail assembly being part of a handle assembly portion of the device shown in FIG. 1A;

FIG. 8 is an isometric view of the first release ring on the first slider;

FIG. 13A is a sectional isometric view of a handle portion of the device shown in FIG. 12, but with the second release ring and second slider removed for clarity and with the locking ring in a locked condition;

FIG. 13B is a sectional isometric view similar to that of FIG. 13A, but with the locking ring in an unlocked condition;

FIG. 14A is a similar view to that of FIG. 13A, but is a close up view and also shows the second release ring and second slider shown in FIG. 12;

FIG. 14B is a similar view to that of FIG. 14A, but shows the second locking ring in a prematurely unlocked condition;

DETAILED DESCRIPTION

Figure 2A:
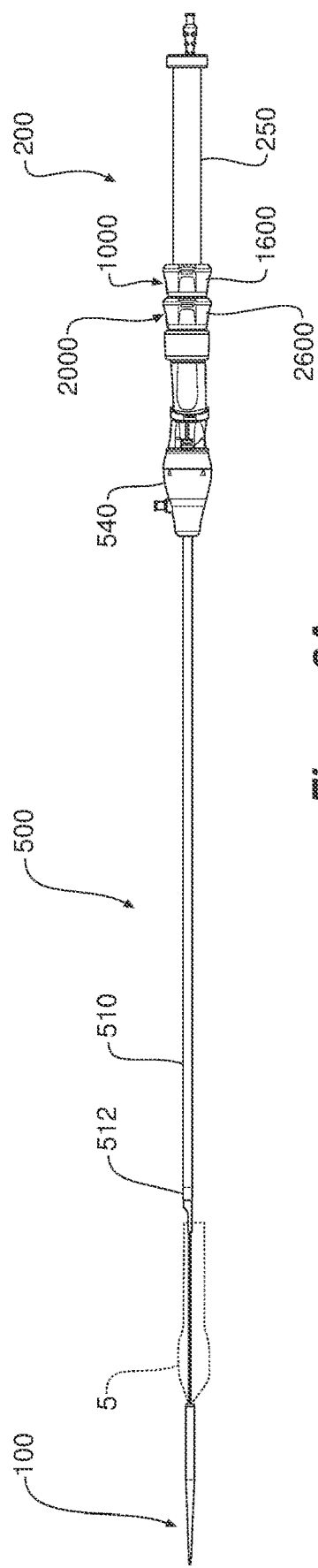
FIG. 2A is a similar side view to that of FIG. 1A but showing a sheath assembly in a retracted position.

Referring to FIGS. 1A, 1B, 2A, 2B, 3A and 3B, an endovascular delivery device 10 for delivering an endograft 5 is shown. At a distal end 18 of the delivery device is a handle assembly 200. According to an embodiment of the invention, a line pull assembly is provided and, in this case, forms part of the handle assembly 200. FIGS. 5A to 5C, 6A to 6C, 7, 8, 9A to 9D, 10, 11A to 11C show the line pull assembly in detail. While the line pull assembly will have many applications, in the embodiments illustrated, the line pull assembly is a wire pull assembly that actuates a trigger wire such as the diameter reducing tie trigger wire 1032 shown in FIGS. 4, 5A, 5B and 6C. This trigger wire 1032 extends from the line pull assembly reducing trigger wire distal end piece 1038 shown in FIG. 6C to an endograft in the form of a stent graft 5 shown in FIG. 4. In other embodiments, the line pull assembly may be used for other purposes on other prosthetic delivery devices.

The line of the line pull assembly is a constructed from a single strand of wire in the embodiments illustrated. In other embodiments the line may be a stranded construction and may be made from non-wire materials including suitable plastic materials.

Figure 5A:
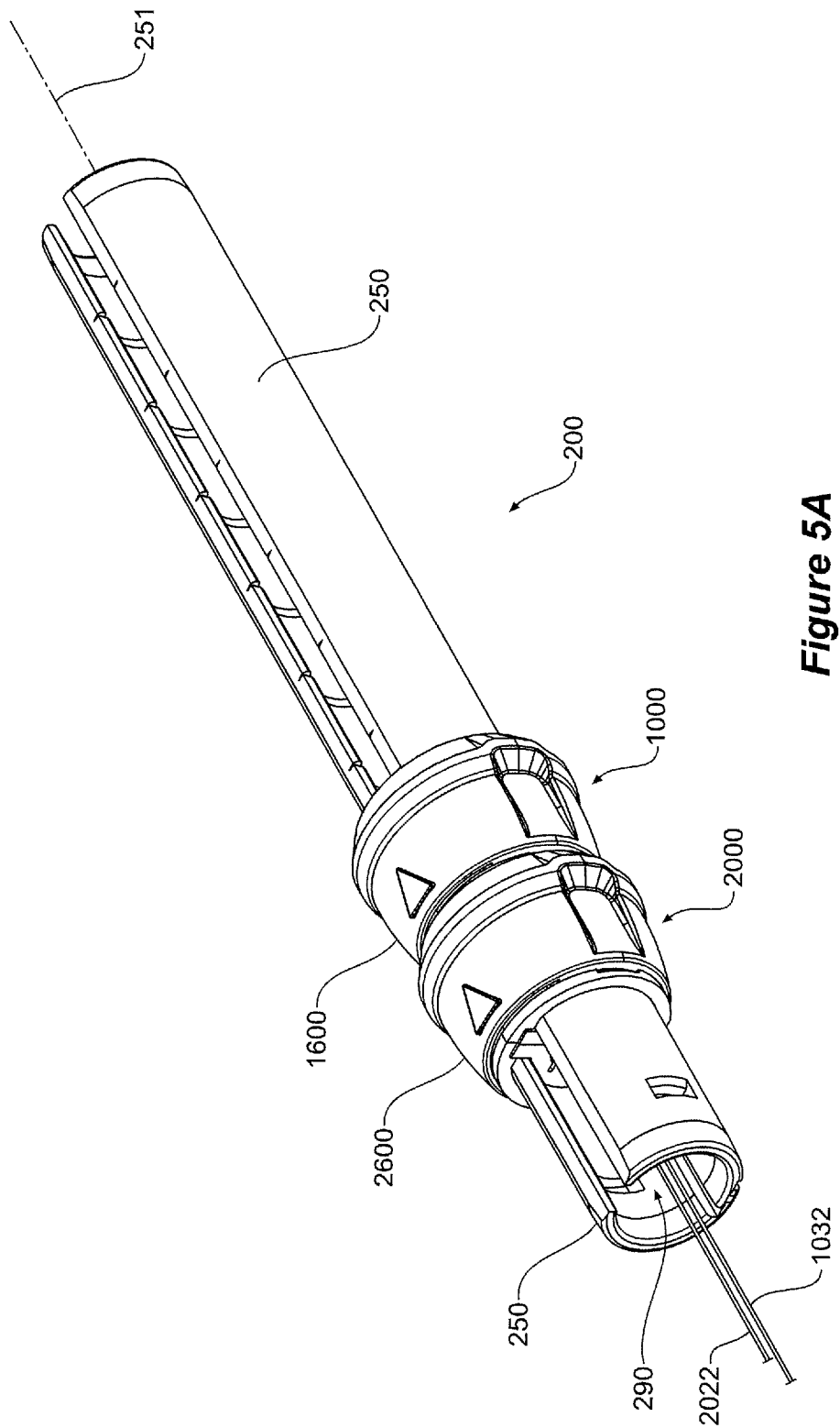
FIG. 5A is an isometric view of a handle portion of the device shown in FIG. 1A, providing detail of a line pull assembly.
Figure 5B:
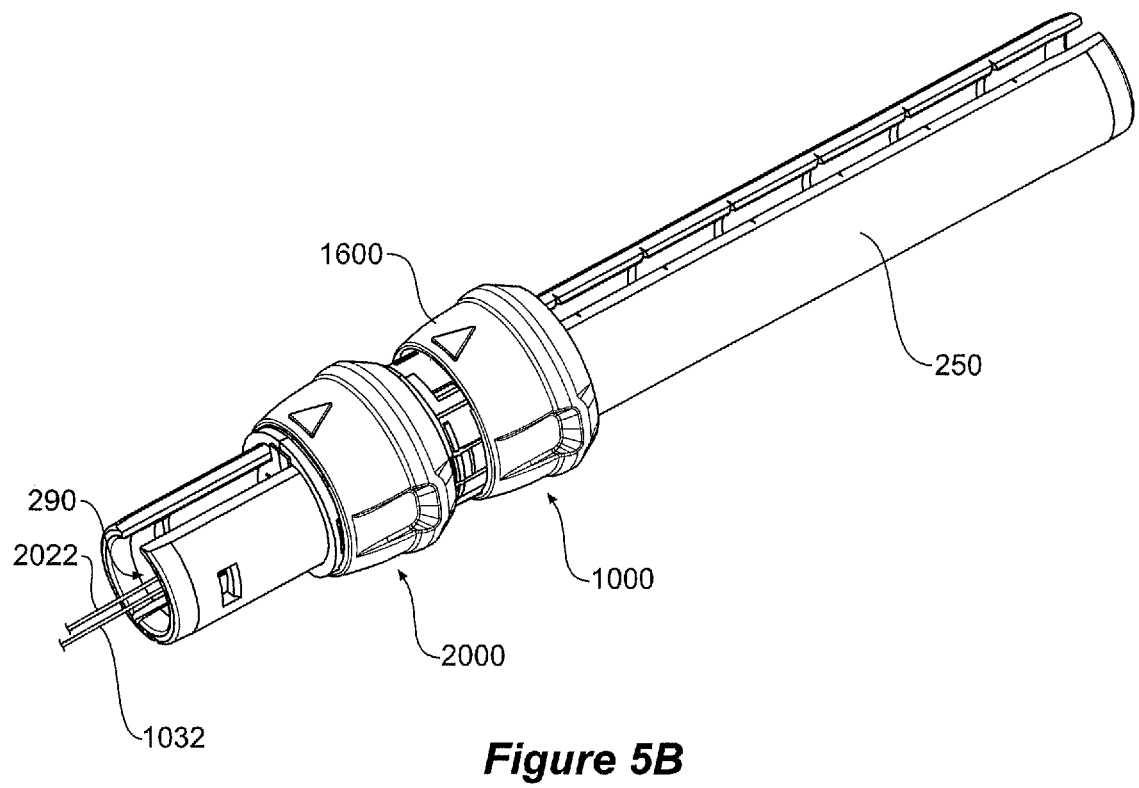
FIG. 5B is a similar view to that of FIG. 5A, but shows a first release ring on a first slider in a released condition.
Figure 5C:
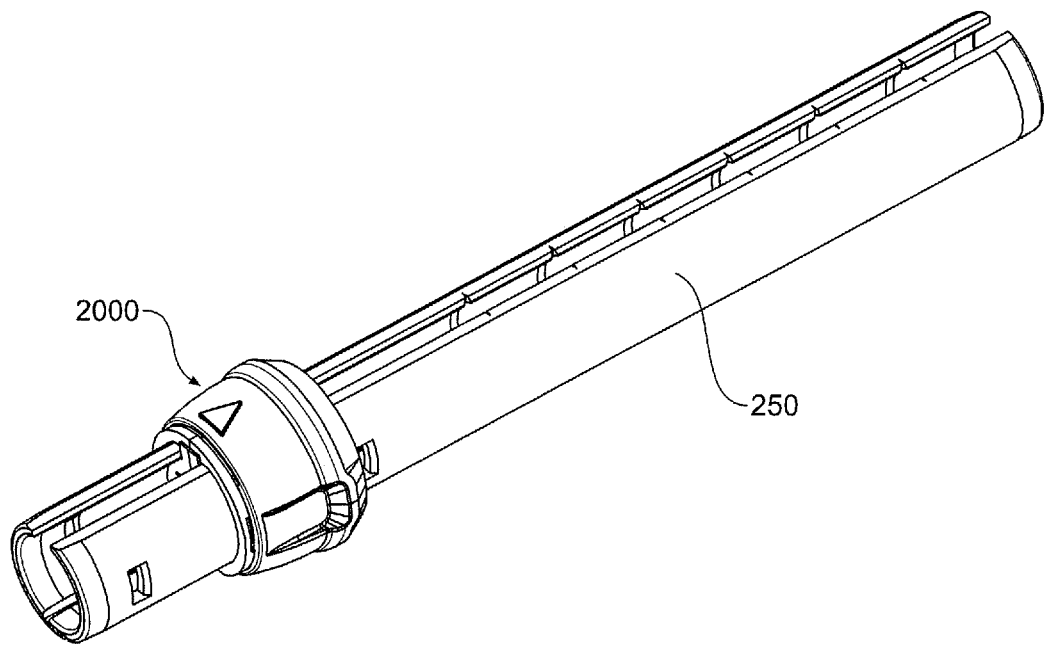
FIG. 5C is a similar view to that of FIG. 5B, but shows a second release ring and second slider ready for sliding movement after the first release shown in FIG. 5B has been slid distally (in this figure, the first slider has been omitted for clarity)
Figure 6A:
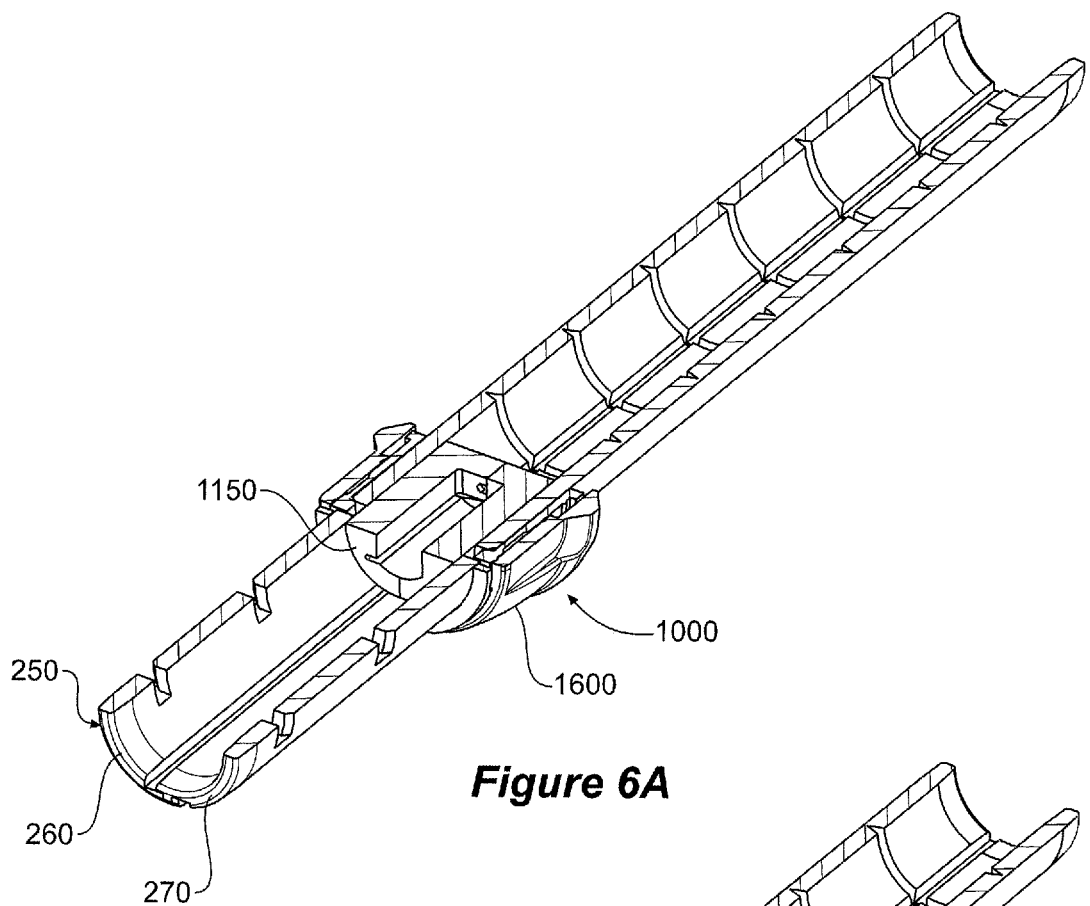
FIGS. 6A to 6C are sectional isometric views of a handle portion of the device shown in FIG. 1A, but with the second release ring and second slider removed for clarity.
Figure 6B:
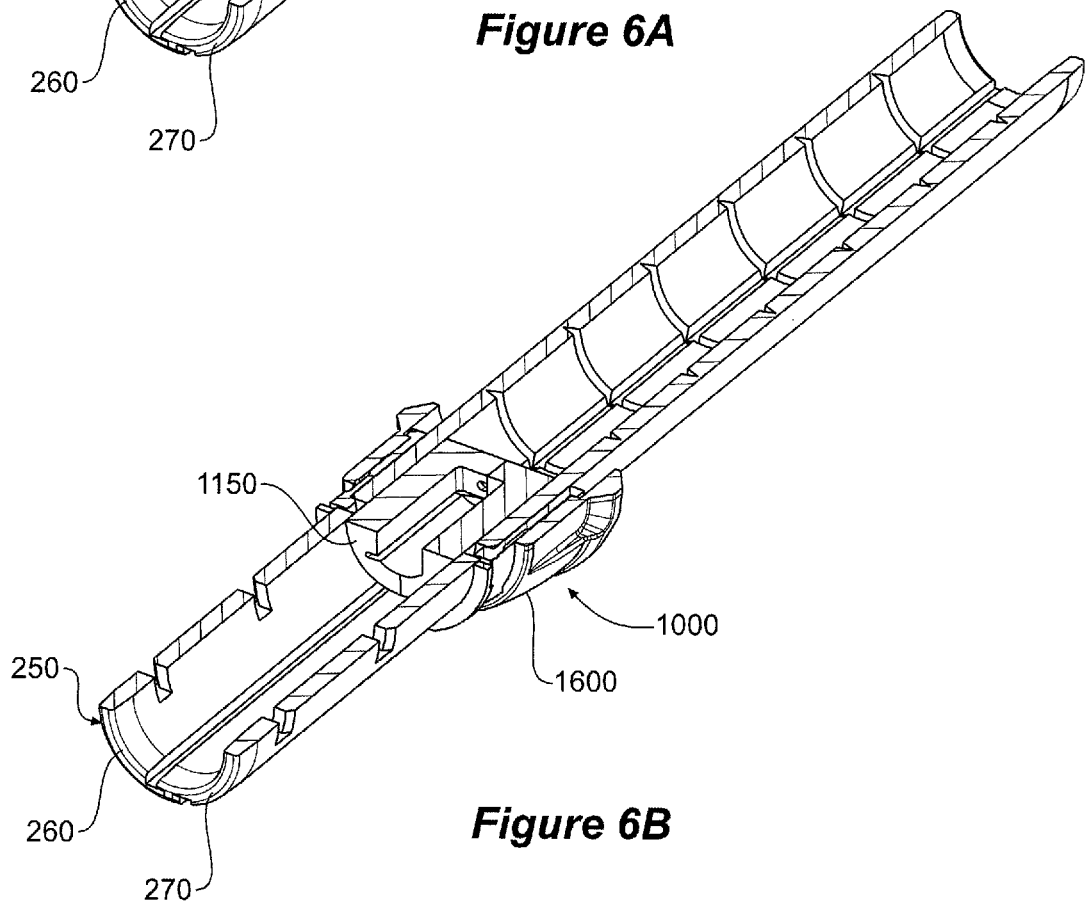
Figure 6C:
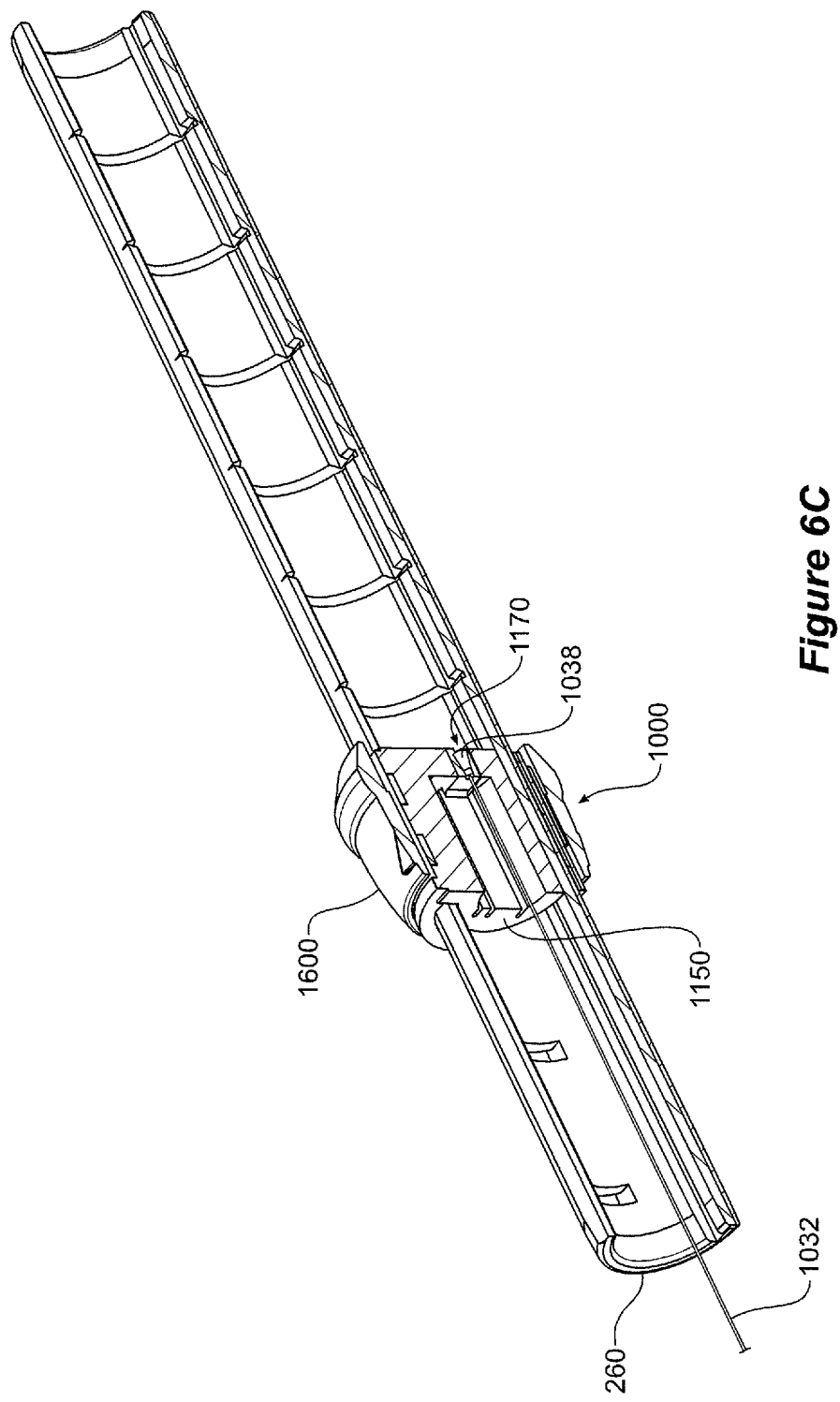

Referring again to FIG. 5A, it can be seen that the line pull assembly comprises a rail assembly 250 defining an internal rail cavity 290 and having a longitudinal axis 251. The line pull assembly also includes a first-hand grippable slider assembly 1000, the first slider assembly 1000 mounted to the rail assembly 250 for relative sliding movement with respect to the rail assembly 250 along the longitudinal axis 251. The first slider assembly comprises a body 1100 slidably mounted to the rail assembly 250. Now turning to FIGS. 6A, 6B and 6C, it can be seen that the body 1100 has an inner body portion 1150 within the rail cavity 290. The inner body portion 1150 comprises a line receiver 1170 which is more clearly shown in FIGS. 6C and 9D. The line receiver 1170 is connected to a pullable line 1032, in the form of a diameter reducing tie trigger wire 1032 as is shown in FIG. 6C. The trigger wire 1032 is also shown in FIGS. 4, 5A and 5B.

Figure 4:
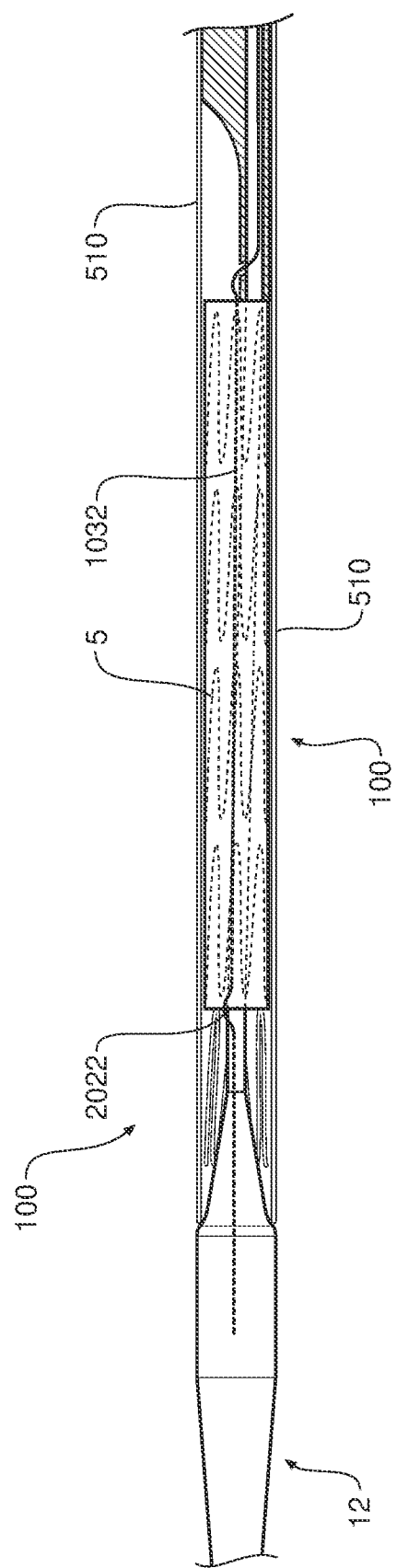
FIG. 4 is a detailed view of a proximal portion of the device shown in FIG. 1B.

Any movement of the slider assembly 1000 and its inner body portion 1150 along the longitudinal axis 251 in a distal direction creates a pulling force along the pullable line 1032 which is connectable to the proximal end 12 of the delivery device 10, as can be seen most clearly in FIG. 4. While in FIG. 4, the line 1032 is a diameter reducing tie trigger wire, sometimes referred to as a reducing trigger wire. In other applications the line 1032 may be a proximal or distal release wire for an endograft 5 or may be used for other purposes.

The line pull assembly 50 also includes a release ring 1600 that is mounted around the rail assembly and is operably connected to the inner body portion 1150. This release ring 1600 is shown in many of the drawings including FIGS. 1A, 2A and 3A and 5A and 5B. The release ring 1600 is slidably movable with respect to the inner body portion 1150 along the longitudinal axis 251 from a locked position shown in FIG. 5A to an unlocked position shown in FIG. 5B. The release ring 1600 is hand operable.

As will be apparent from the more detailed description below, the first slider assembly 1000 is locked against sliding movement with respect to the rail assembly 250 until the release ring 1600 is moved to the unlocked position shown in FIG. 5B. When in the unlocked position, the inner body portion 1150 is slidably movable by sliding movement of the release ring 1600 to transfer a pulling motion and force through the line receiver 1170 to the line 1032, as is shown in FIG. 5B and in FIGS. 11B and 11C.

Figure 9A:
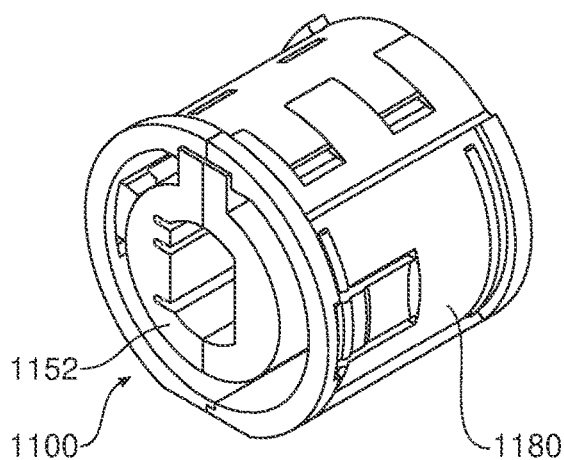
FIGS. 9A and 9B are isometric and end views respectively of a body being part of the slider assembly.
Figure 9B:
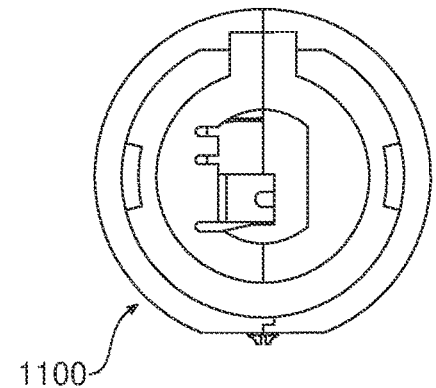
Figure 10:
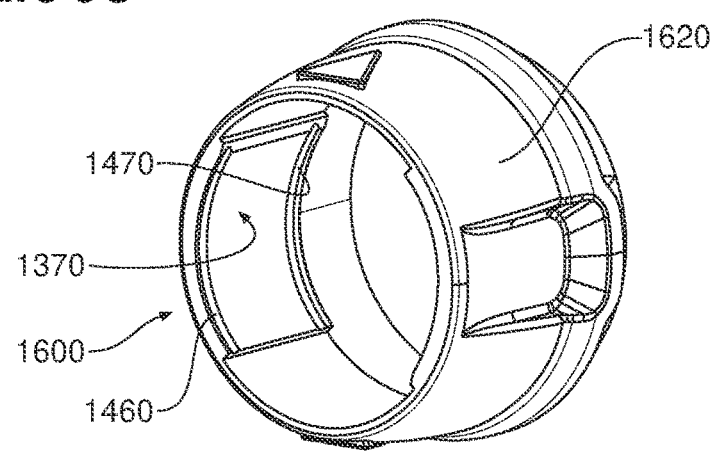
FIG. 10 is an isometric sectional view of the first release ring shown in FIG. 5B (and others)

As can be seen in FIG. 10 when read with FIG. 9A, the release ring 1600 comprises a hand-gripable external annular surface 1620 extending 360 degrees around an outer body portion 1180 of the body 1100, whereby the release ring is hand-actuatable irrespective of its orientation about the longitudinal axis.

Referring to the three FIGS. 11A to 11C again, the progressive steps of actuating the release ring and then pulling the line receiver 1170 (and hence the line 1032) can be seen clearly. First, sliding the release ring 1600 distally along the longitudinal axis 251 (from the position shown in FIG. 11A to the position shown in FIG. 11B) can occur. Second, further sliding of the release ring 1600 distally along the longitudinal axis 251 can occur now that the lock is unlocked causing the inner body portion 1150 to move distally from the position shown in FIG. 11B to the position shown in FIG. 11C. This can be done without the operator needing to move his or her grip as the release ring 1600 performs both the unlocking function and the function of moving the actual first slider 1000 after its release from the rail assembly 250.

The release ring 1600 comprises a hand grippable external annular surface 1620, as is most clearly shown in FIG. 10. This surface extends 360 degrees around an outer body portion 1180 of the body portion 1100. This allows the release ring 1600 to be hand actuatable irrespective of its orientation about the longitudinal axis 251. This is important because, during a procedure, it is advantageous for the surgeon not to have to move his or her hand into an uncomfortable position to achieve the necessary activation of the device. Furthermore, the shape of the actuator is such that it does not provide a catching risk.

Figure 9C:
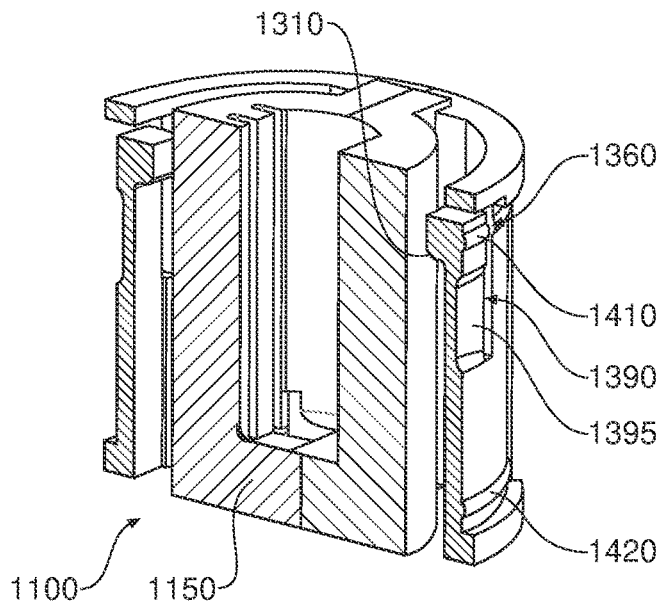
FIG. 9C is an isometric sectional view of the body shown in FIGS. 9A and 9B.
Figure 9D:
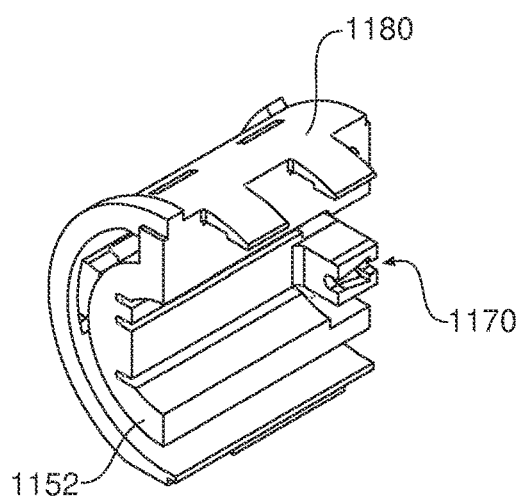
FIG. 9D is an isometric view showing an inner body half of the body shown in FIGS. 9A and 9B.

A first detent pair between the body 1100 and the release ring 1600, is provided. The first detent pair is arranged and constructed to hold the release ring 1600 in the locked position shown in FIGS. 5A and 11A. How this first detent pair functions can be seen in FIGS. 9C, 10 and 11A to 11C. The first detent pair comprises a first detent projection 1410 as can be seen in FIG. 9C and a first detent recess 1460 as can be seen in FIG. 10. How the first detent projection 1410 and the first detent recess 1460 interact as a first detent pair is most easily seen in FIGS. 11A to 11C.

A second detent pair between the body 1100 and the release ring 1600 is also provided for the embodiment of the invention illustrated. The second detent pair is arranged and constructed to hold the release ring in the unlocked position shown in FIGS. 5B and 11B and 11C. The second detent pair comprises a second detent projection 1420 shown in FIG. 9C and a second detent recess 1470 as can be seen in FIG. 10. Again, how the second detent projection 1420 and the second detent recess 1470 interact as a second detent pair is most easily seen in FIGS. 11A to 11C.

Figure 11A:
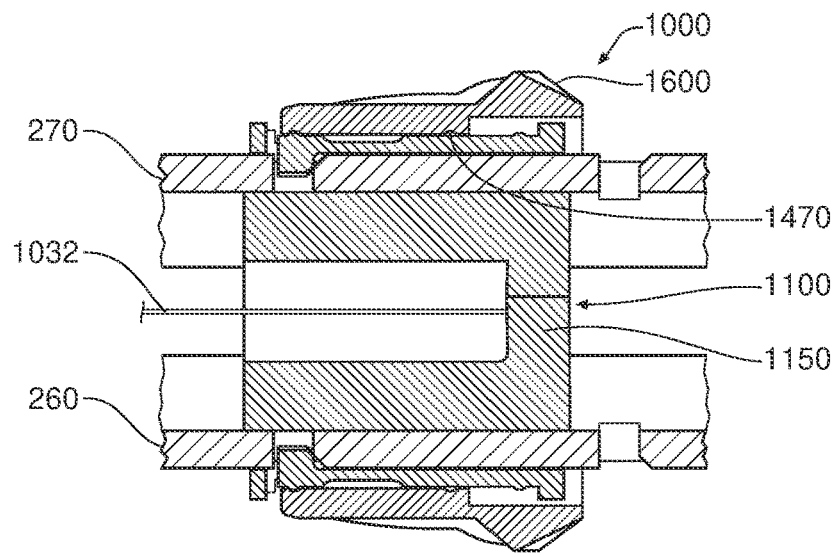
FIG. 11A is a sectional view showing the first slider assembly in a locked position.
Figure 11B:
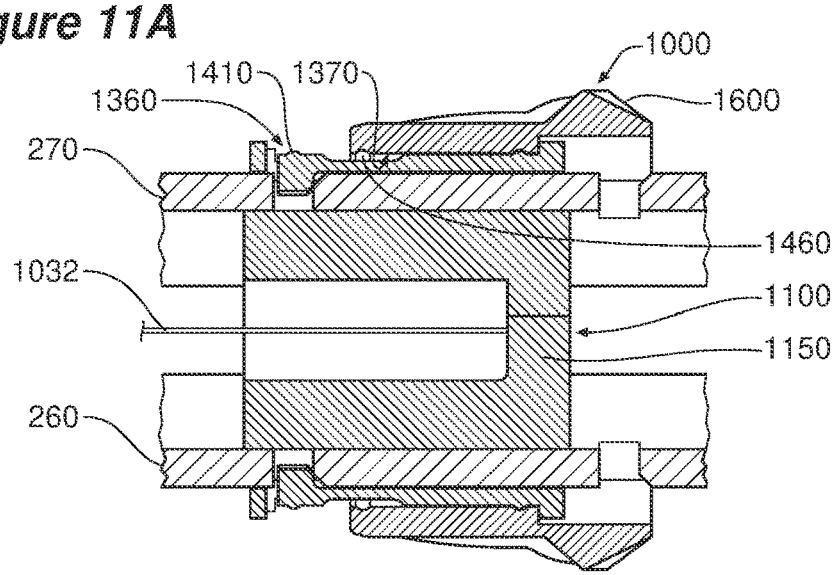
FIG. 11B is a sectional view similar to that of FIG. 11A, but showing the first slider assembly in an unlocked position.
Figure 11C:
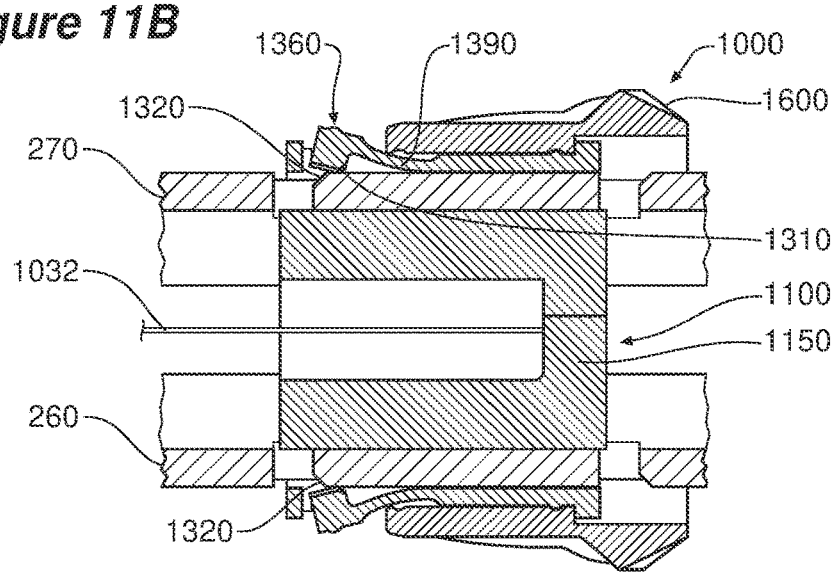
FIG. 11C is a sectional view similar to that of FIGS. 11A and 11B, but showing the first slider assembly in an unlocked position and moved distally.

A locking assembly for locking the first slider assembly 1000 against sliding movement with respect to the rail assembly 250 is also provided. FIG. 11A, a sectional view, shows the first slider assembly in a locked position. Then FIG. 11B shows the first slider assembly in an unlocked position and finally FIG. 11C shows the first slider assembly in an unlocked position and moved distally. From these Figures, it can be seen that the locking assembly comprises a pair of cooperating surfaces including a first surface 1310 and a second surface 1320. The second surface 1320 is shown within a cut-out or slot through the rail halves 260 and 270 in FIG. 7. The first surface 1310 can be seen in FIG. 9C and in FIG. 11C. However the interaction of these surfaces is most easily seen in the progressive movements between FIGS. 11A and 11C. The first surface 1310 of the pair of cooperating surfaces is radially movable with respect to the longitudinal axis 251 and has been displaced radially outwards in FIG. 11C from its position shown in FIGS. 11A and 11B.

In FIG. 11A, it can be seen that the first and second surfaces are engaged in the locked position so as to limit relative axial movement. More specifically, in the configuration shown in FIG. 11A, an initial configuration, the release ring 1600 is in a position that prevents substantial radial movement of the first surface 1310. More specifically, the locking assembly further comprises a third surface 1360 on the flexible arm 1390 and facing radially outward with respect to the longitudinal axis 251, as can be seen in FIGS. 11B and 9C, as well as a proximal blocking face 1370 on the release ring 1600 as can be seen in FIGS. 10 and 11B for instance. In the locked position, the third surface 1360 is blocked from radially outward movement by the internal proximal blocking face 1370 on the release ring 1600, thereby limiting radial movement of at least one of the first and second surfaces 1310, 1320 with respect to the other of the first and second surfaces 1310, 1320 of the pair of co-operating surfaces. As already described, in the embodiment shown in FIGS. 5A to 11C, the first surface 1310 moves radial with respect to the longitudinal axis 251. It is shown displaced radially outwards in FIG. 11C from its position shown in FIGS. 11A and 11B.

As can be seen in FIG. 9C, the flexible arm 1390 is attached to, or forms part of, the body 1100 and includes a necked portion 1395 that extends from, or forms a part of the external body portion 1180. The thickness of the necked portion 1395 can be selected to provide the optimum level of resistance against flexing. The material specifications for the body 1100 and its necked portion 1395 are chosen to provide resilience.

So far a first hand-gripable slider assembly 1000 and its interaction with the rail assembly 250 has been described. However, FIGS. 1A to 5B, illustrate a second hand-gripable slider assembly 2000 which is desirably provided adjacent to the first slider assembly 1000.

Referring now to FIGS. 5A and 5B, it can be seen that the second hand-gripable slider assembly 2000 is mounted on the rail assembly 250 adjacent to the first slider assembly 1000 such that relative sliding movement of the second slider assembly with respect to the rail assembly is blocked by the first hand-gripable slider assembly 1000 in the initial configuration of FIGS. 1A, 1B, 2A, 2B and 5A. The second hand-gripable slider assembly 2000 is only slidable with respect to the rail assembly 250 after the first hand-gripable slider assembly 1000 has been slid away from the second hand-gripable slider assembly 2000. This is because, in the initial configuration, as the device intended to be delivered to the surgeon for a procedure, the second slider assembly 2000 is located hard up against, or at least very close to, the first slider assembly 1000. This is important because it prevents accidental premature actuation of the second slider 2000.

Figure 12:
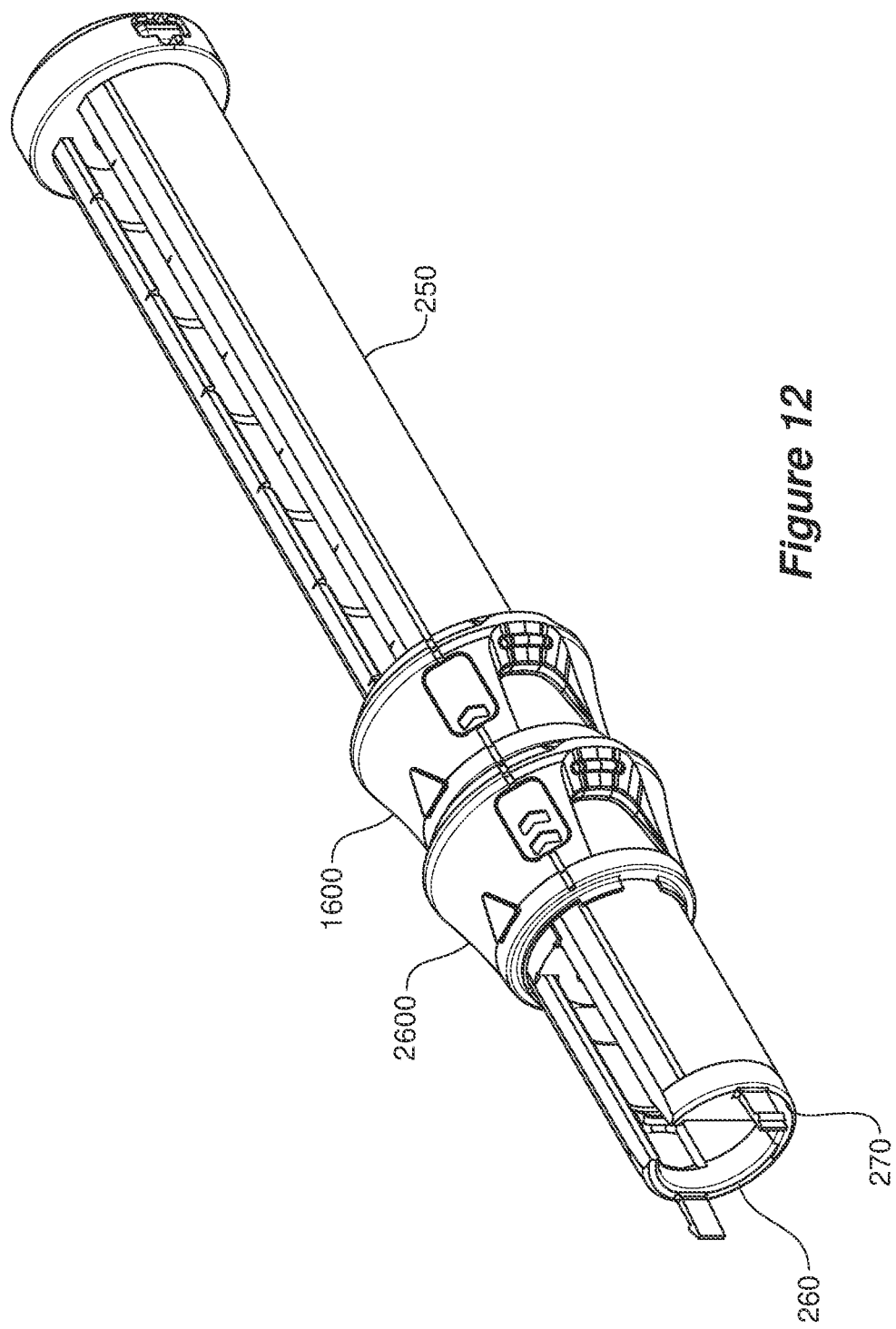
FIG. 12 is an isometric view of a handle portion of the device shown in FIG. 1A, but with an alternative line pull assembly to that shown in FIGS. 5A to 11C.

FIG. 12 is an isometric view of a handle portion of the device shown in FIG. 1A, but with an alternative line pull assembly to that shown in FIG. 5A to 11C. This alternative will be referred to as a second embodiment of the invention.

With the second embodiment of the invention, a significant design difference is that the flexible arm is attached to, or forms part of, the rail assembly 250 as can be seen in FIGS. 13A and 13B.

Figure 19A:
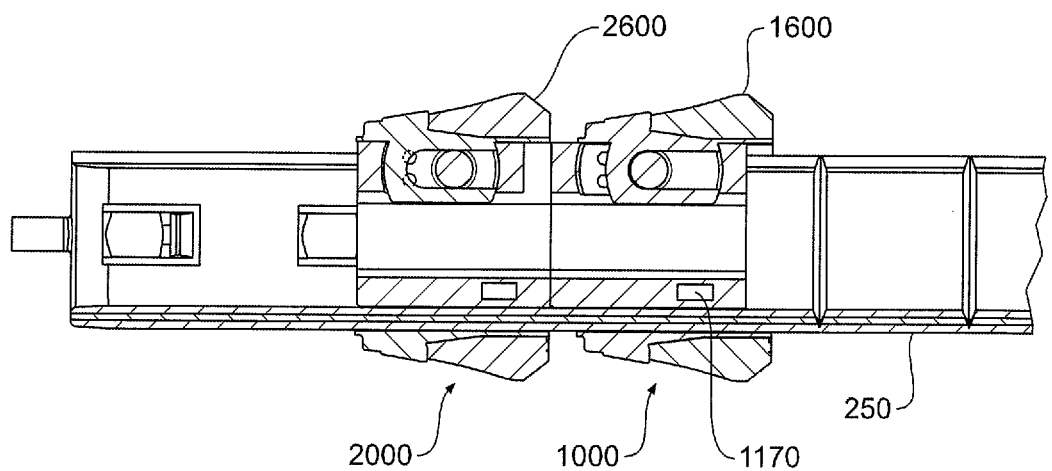
FIG. 19A is a cross sectional view of a handle portion of the device shown in FIG. 12, showing the first release unlocked.
Figure 19B:
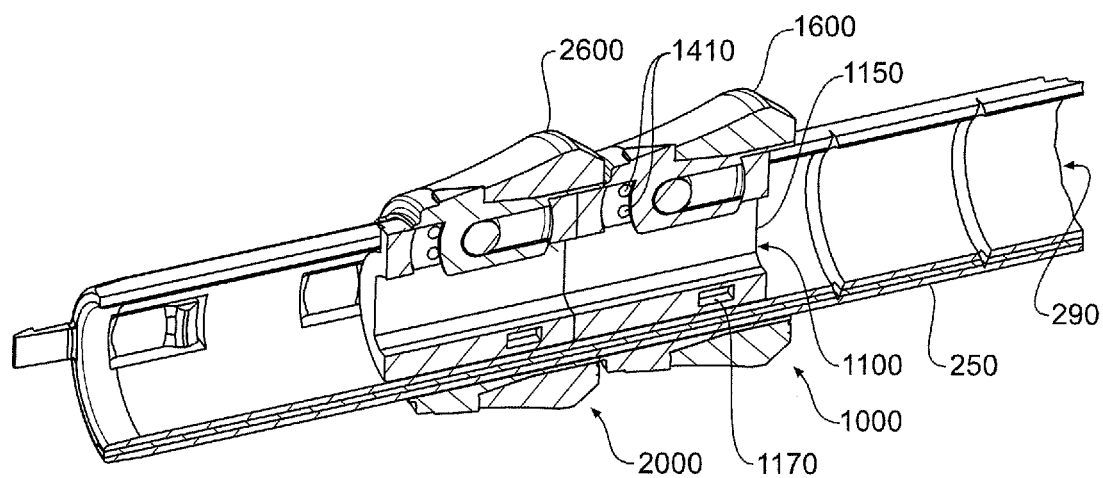
FIG. 19B is a similar view to that of FIG. 19A, but is an isometric cross sectional view that shows the second locking ring in a prematurely unlocked condition as is shown in FIG. 14B.

Now turning to FIGS. 19A and 19B, it can be seen that the first slider assembly 1000 has a body 1100 which has an inner body portion 1150 within the rail cavity 290. The inner body portion 1150 comprises a line receiver 1170. The line receiver 1170 is connected to a pullable line 1032, in the form of a diameter reducing tie trigger wire 1032. The line receiver 1170 and the pullable line 1032 are very similar, if not identical to the same components of the first embodiment of the invention described above.

With the second embodiment of the invention, a further safety feature is shown in the form of a distal blocking face 1380 as will now be explained with reference to FIGS. 14A and 14B. The second hand-gripable slider assembly 2000 comprises a distal blocking face 1380 that is arranged and constructed to prevent the first release ring 1600 slideably moving with respect to the inner body portion 1150 from the locked position to the unlocked position before the first hand-gripable slider assembly 1000 has been slid away from the second hand-gripable slider assembly 2000.

Figure 15A:
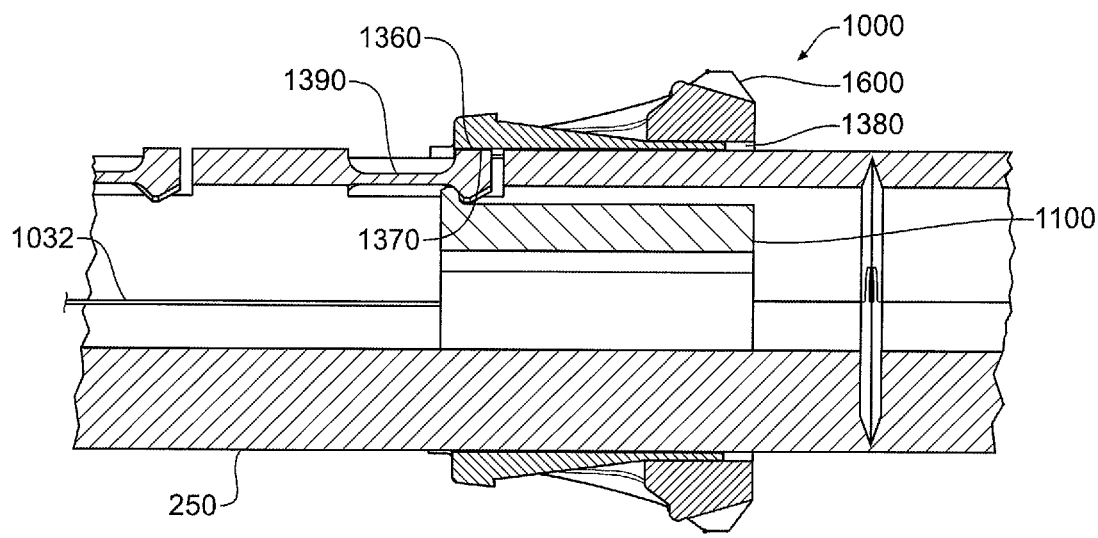
FIG. 15A is a sectional view showing the first slider assembly of FIG. 12 in a locked position.
Figure 15B:
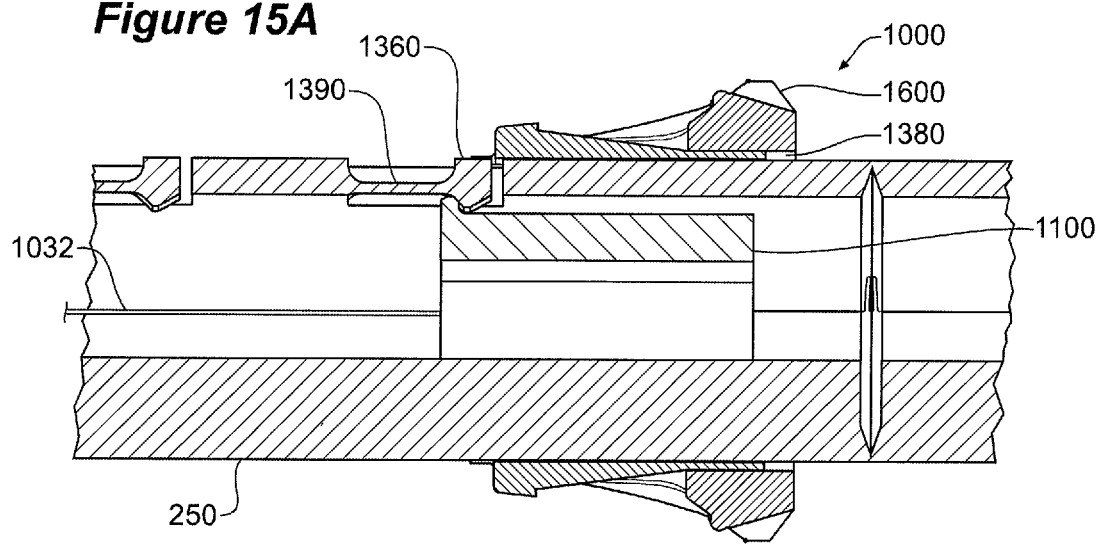
FIG. 15B is a sectional view similar to that of FIG. 15A, but showing the first slider assembly in an unlocked position.
Figure 15C:
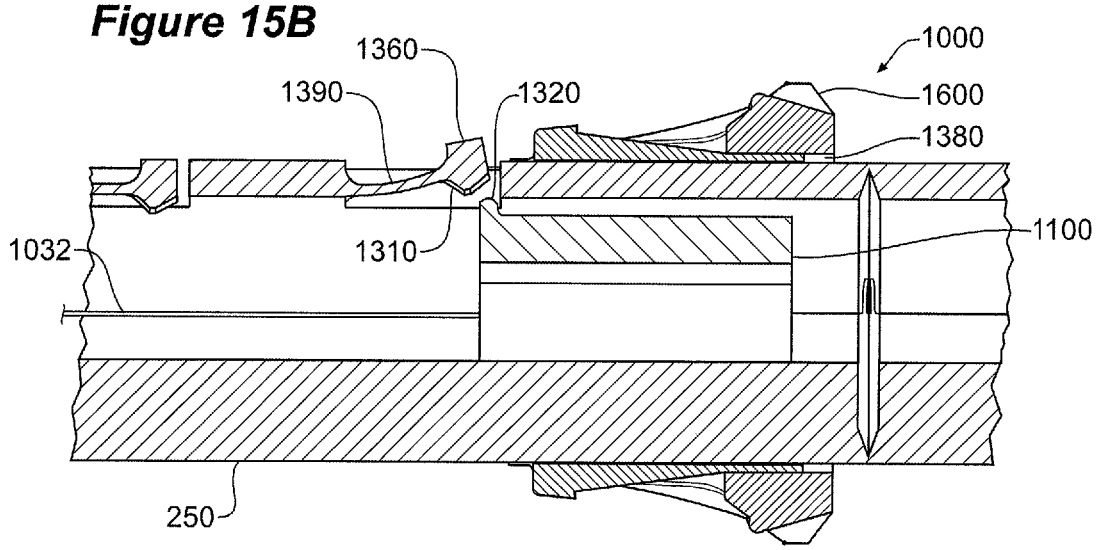
FIG. 15C is a sectional view similar to that of FIGS. 15A and 15B, but showing the first slider assembly in an unlocked position and moved distally.

Referring to the three FIGS. 15A to 15C, the progressive steps of actuating the release ring and then pulling the line receiver 1170 (and hence the line 1032) for this embodiment of the invention can be seen clearly.

As is the case for the first embodiment, the first surface 1310 of the second embodiment is again on a flexible arm 1390 as is clearly shown in FIG. 15A. The flexible arm 1390 is again desirably flexible and resilient such that it acts as a spring biasing it into the position shown in FIGS. 15A and 15B. The flexible arm 1390 is connected to the rail assembly 250, or more specifically the one of the two halves 260, 270 of the rail assembly 250. In other embodiments, not shown, the two halves 260, 270 of the rail assembly 250 may not exist and a single unitary rail may be provided.

Figure 16:
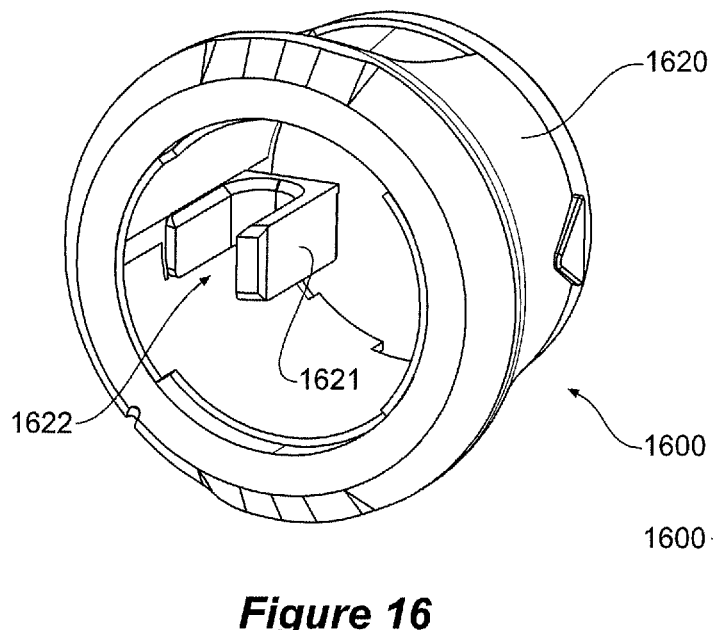
FIG. 16 an isometric view of a release ring of the first slider assembly shown in FIGS. 14A, 14B and 15A to 15C.
Figure 17:
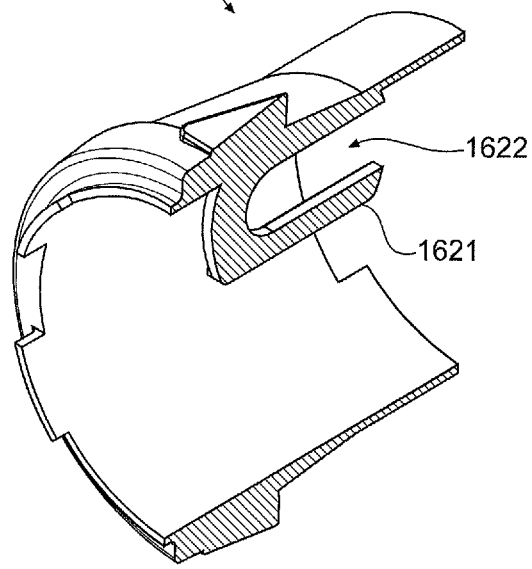
FIG. 17 is a sectional view of the release ring shown in FIG. 16.
Figure 18:
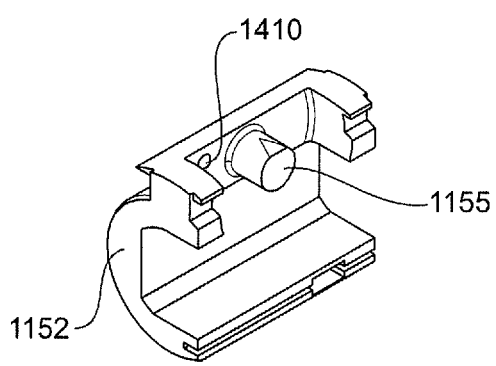
FIG. 18 is an isometric view of an inner body portion half of a body forming part of the first slider assembly shown in FIGS. 14A, 14B and 15A to 15C.

FIG. 16 an isometric view of a release ring of the first slider assembly shown in FIGS. 14A, 14B and 15A to 15C. FIG. 17 is a sectional view of the release ring shown in FIG. 16. A guide 1621 that provides a guide recess 1622 is clearly seen in FIGS. 16 and 17. A post 1155 extending from the inner body portion half 1152 is shown in FIG. 18. This post 1155 is slidably moveable within the guide 1621 is most clearly seen in FIGS. 17A and 19B.

With the second embodiment of the invention, a significant further difference over the first embodiment is that a different detent mechanism is provided between the body 1100 and the release ring 1600, however the detent mechanism is again arranged and constructed to hold the release ring 1600 in the locked position against unintended or inadvertent movement. This detent mechanism comprises a first detent pair arranged and constructed to hold the release ring 1600 in the locked position, which is most clearly shown in FIGS. 19A and 19B. FIG. 19A is a cross sectional view of a handle portion of the device shown in FIG. 12, showing the first release unlocked. FIG. 19B is a similar view to that of FIG. 19A, but is an isometric cross sectional view that shows the second locking ring in a prematurely unlocked condition as is shown in FIG. 14B.

The first detent pair shown in FIG. 19B comprises a pair of first detent projections 1410, although in other embodiment there may be just as single first detent projection 1410.

A second detent pair between the body 1100 and the release ring 1600 is also provided, the second detent pair arranged and constructed to hold the release ring 1600 in the unlocked position, as shown in FIG. 19A. With this embodiment, the second detent pair utilizes the same first detent projections 1410.

For the purposes of understanding the principles of the invention, reference will now be made to the embodiments illustrated in the drawings, and specific language will be used to describe them. It is to be understood that the Figures are, in some cases, schematic and do not show the various components in their actual scale. In many instances, the Figures show scaled up components to assist the reader.

Operation of the Device

Use or operation of the delivery device 10 that includes the line pull assembly described above will now be described. The operation will be described with reference to the first embodiment of the invention shown in FIG. 1A to FIG. 11C.

Referring first to FIG. 1A and its companion FIG. 1B, the delivery device 10 is shown together with a sheath assembly 500 in a configuration ready for use.

Typically, one of the first major steps in a procedure undertaken by a vascular surgeon would be to introduce a guide wire into a blood vessel, such as the femoral artery, using the Seldinger technique. This technique involves creating a surgical opening in the vessel of the needle and inserting a wire guide into the vessel through a bore of the needle. The needle is then withdrawn leaving the guide wire in place. The delivery device 10, as shown in FIGS. 1A and 1B, is then inserted over the guide wire and into the vessel.

Figure 2B:
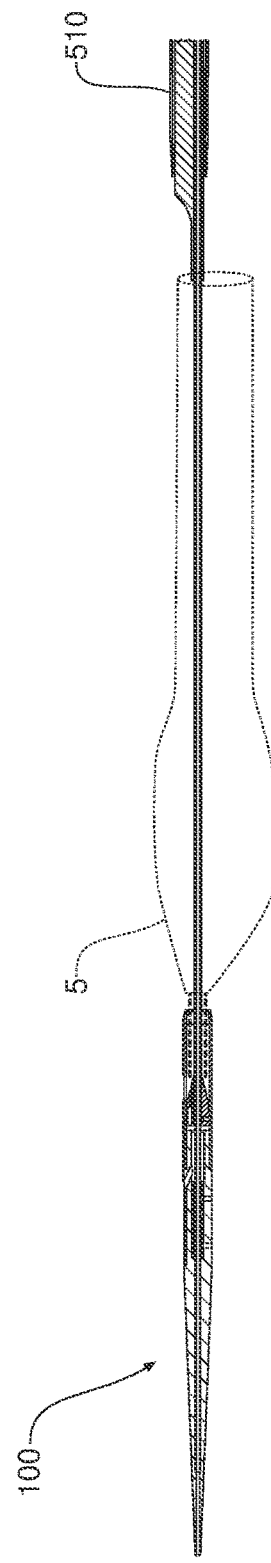
FIG. 2B shows a proximal end of the device of FIG. 2A.
Figure 3A:
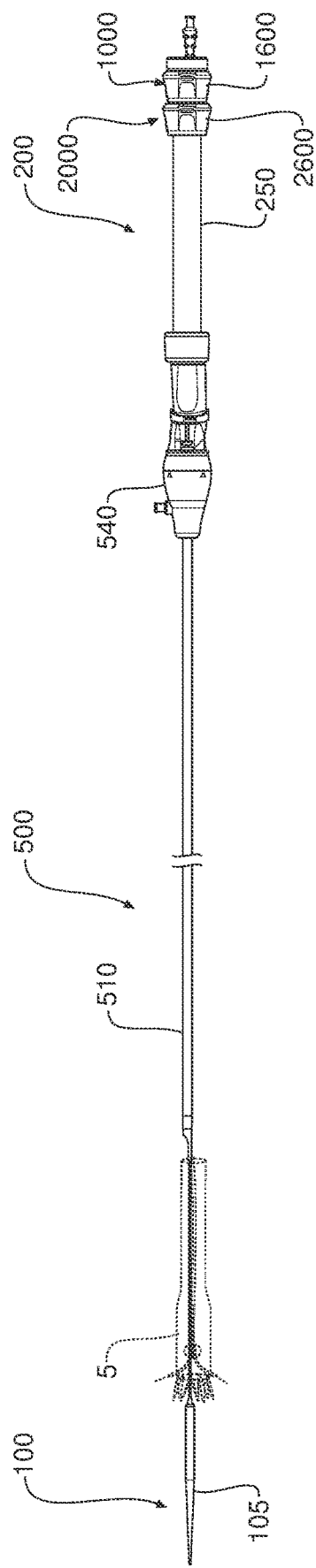
FIG. 3A is a similar side view to that of FIG. 2A but showing an endograft in a partially released condition.
Figure 3B:
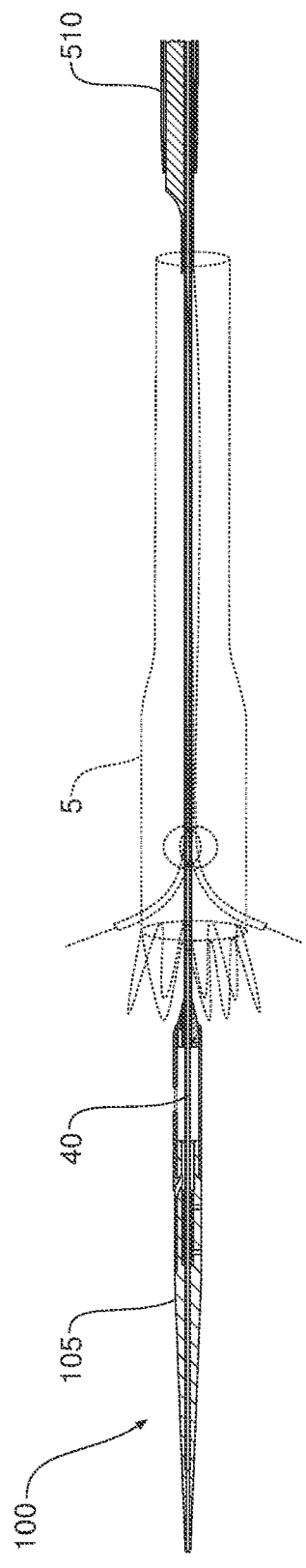
FIG. 3B shows a proximal end of the device of FIG. 3A.

Once the surgeon has positioned the proximal end 12 of the delivery device 10 near the target delivery area for the endograft 5, the sheath assembly 500 can be withdrawn to the position shown in FIGS. 2A and 2B. In this position, the sheath 510 of the sheath assembly 500 has been pulled back over the compressed endograft for stent graft 5 so as to expose it, as is shown in FIG. 2B. This step is conducted by "grounding" the handle 200 while pulling the valve body 540 of the sheath assembly 500 in a distal direction (away from the patient).

Typically, a next step in operating the delivery device 10 would be causing the stent graft to expand from its reduced condition to an expanded condition. This next step causes removal of the reducing trigger wire, the distal end of which can be seen most clearly in FIG. 4. In order to commence this step, the surgeon grips the release ring 1600 of the first slider assembly 1000 in its position shown in FIG. 5A. He or she then slides the release ring 1600 distally breaking out of the first detent described above to release the first slider assembly from its locked position (where it is locked against sliding movement with respect to the rail assembly as has been described above). This sliding movement can be seen in the progression from the positions shown in FIGS. 5A and 5B.

Next, the surgeon or operator continues to slides the release ring 1600 and now the entire first slider assembly along the rail assembly 250 in a distal direction, the commencement of which is shown in FIG. 5B. This has the effect of pulling the reducing trigger wire 1032. The reducing trigger wire 1032 is pulled in a distal direction and its proximal end, shown in FIG. 4, moves free from the endograft 5 allowing it to expand. It can also be seen that this step moves the reducing trigger wire release slider assembly 1000 from its position hard up against the adjacent second slider 2000, which in this embodiment is a proximal trigger wire release slider assembly 2000 to a position longitudinally spaced apart from adjacent proximal trigger wire release slider 1000.

Typically, the next step in the procedure would be to release the proximal trigger wire 2022 illustrated in FIGS. 5A and 4.

This is done by actuating the second release ring 2600 which functions in the same way as the first release ring 1600 already described. Importantly, this cannot be done out of sequence. That is, the second slider assembly 2000 cannot be moved before the first slider assembly 1000.

Movement of the slider assembly 2000 causes the proximal trigger wire 2022 to be detached from the tip assembly 100.

The remainder of the procedure may include actuation of a tip assembly actuator as is described in the applicant's earlier U.S. provisional patent application 62/594,911 filed on 5 Dec. 2017.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

What is claimed is:

1. A line pull assembly for a prosthetic delivery device, the line pull assembly comprising:
   a rail assembly defining an internal rail cavity and having a longitudinal axis; and
   a first hand-gripable slider assembly, the first hand-gripable slider assembly mounted to the rail assembly for relative sliding movement with respect to the rail assembly along the longitudinal axis, the first hand-gripable slider assembly comprising:
      a body slidably mounted to the rail assembly, the body having an inner body portion within the rail cavity, the inner body portion comprising a line receiver disposed within the body and connected to the inner body, the line receiver receiving a pullable line; and
      a release ring mounted around the rail assembly and operably connected to the inner body portion, the release ring slideably moveable with respect to the inner body portion along the longitudinal axis from a locked position to an unlocked position,
   wherein, the first hand-gripable slider assembly is locked against sliding movement with respect to the rail assembly until the release ring is moved to the unlocked position and,
   wherein, in the unlocked position, the inner body portion is slideably moveable with the line receiver by sliding movement of the release ring to pull the line receiver.

2. The line pull assembly as claimed in claim 1 wherein the release ring comprises a hand-gripable external annular surface extending 360 degrees around an outer body portion of the body,
   whereby the release ring is hand-actuatable irrespective of its orientation about the longitudinal axis.

3. The assembly as claimed in claim 1 comprising a first detent pair between the body and the release ring, the first detent pair arranged and constructed to hold the release ring in the locked position.

4. The line pull assembly as claimed in claim 3 comprising a second detent pair between the body and the release ring, the second detent pair arranged and constructed to hold the release ring in the unlocked position.

5. The line pull assembly as claimed in claim 3 wherein the first detent pair comprises a first detent projection and a first detent recess and the second detent pair comprises a second detent projection and a second detent recess.

6. The line pull assembly as claimed in claim 2 comprising a locking assembly, the locking assembly comprising a pair of co-operating surfaces including a first surface and a second surface,
   wherein the first surface of the pair of co-operating surfaces is radially movable with respect to the longitudinal axis in the unlocked position so as to allow relative movement between the first surface and the second surface, and
   wherein, in the locked position, the first and second surfaces are engaged in the locked position so as to limit relative axial movement.

7. The line pull assembly as claimed in claim 6 wherein the first surface is on a flexible arm connected to either one of the first hand-gripable slider assembly and the rail assembly and the second surface is on the other of the first slider assembly and the rail assembly.

8. The line pull assembly as claimed in claim 7 wherein at least one of the first and second surfaces of the pair of co-operating surfaces is radially moveable with respect to the other of the first and second surfaces so as to allow disengagement when the release ring is in the unlocked position.

9. The line pull assembly as claimed in claim 8 wherein the locking assembly further comprises a third surface, the third surface on the flexible arm and facing radially outward with respect to the longitudinal axis.

10. The line pull assembly as claimed in claim 9 wherein, the locking assembly further comprises a proximal blocking face on the release ring and wherein, in the locked position, the third surface is blocked from radially outward movement by the proximal blocking face on the release ring, thereby limiting radial movement of at least one of the first and second surfaces with respect to the other of the first and second surfaces of the pair of co-operating surfaces.

11. The line pull assembly as claimed in claim 7 wherein the flexible arm is attached to, or forms part of, the body and includes a necked portion.

12. The line pull assembly as claimed in claim 7 wherein the flexible arm is attached to, or forms part of, the rail assembly.

13. The line pull assembly as claimed in claim 1 comprising a second hand-gripable slider assembly, the second hand-gripable slider assembly mounted on the rail assembly adjacent to the first slider assembly such that relative sliding movement of the second slider assembly with respect to the rail assembly is blocked by the first hand-gripable slider assembly in an initial configuration, such that the second hand-gripable slider assembly is only slidable with respect to the rail assembly after the first hand-gripable slider assembly has been slid away from the second hand-gripable slider assembly.

14. The line pull assembly as claimed in claim 13 wherein the second hand-gripable slider assembly comprises a distal blocking face, the distal blocking face arranged and constructed to prevent the release ring of the first hand grippable slider assembly slideably moving with respect to the inner body portion from the locked position to the unlocked position before the first hand-gripable slider assembly has been slid away from the second hand-gripable slider assembly.

15. An endovascular delivery device, for delivering an endograft, endovascular the delivery device comprising:
 a handle assembly at a distal end thereof;
 a nose assembly at a proximal end thereof,
 a guide wire catheter extending through the handle assembly, the guide wire catheter being affixed at a proximal end thereof to nose assembly; an endograft receiving portion extending distally with respect to the nose assembly;
 a pullable line extending from the handle assembly to the endograft receiving portion; and
 a line pull assembly, the assembly comprising:
  a rail assembly within the handle assembly defining an internal rail cavity and having a longitudinal axis; and
  a first hand-gripable slider assembly, the first hand-gripablet slider assembly mounted to the rail assembly for relative sliding movement with respect to the rail assembly along the longitudinal axis, the first hand-gripablet slider assembly comprising:
   a body slidably mounted to the rail assembly, the body having an inner body portion within the rail cavity, the inner body portion comprising a line receiver disposed within the body and connected to the inner body portion and the pullable line; and
   a release ring mounted around the rail assembly and operably connected to the inner body portion, the release ring slideably moveable with respect to the inner body portion along the longitudinal axis from a locked position to an unlocked position,
  wherein, the first slider assembly is locked against sliding movement with respect to the rail assembly until the release ring is moved to the unlocked position and,
  wherein, in the unlocked position, the inner body portion is slideably moveable with the line receiver by sliding movement of the release ring to pull the pullable line.

16. The endovascular delivery device as claimed in claim 15 wherein the release ring comprises a hand-gripable external annular surface extending 360 degrees around an outer body portion,
 whereby the release ring is hand-actuatable irrespective of its orientation about the longitudinal axis.

17. The endovascular delivery device as claimed in claim 16 wherein the pullable line is a wire.

18. The endovascular delivery device as claimed in claim 17 wherein the pullable line comprises a reducing trigger wire having a proximal end for releasing diameter reducing ties in the endograft.

19. The line pull assembly as claimed in claim 18 comprising a first detent pair between the body and the release ring, the first detent pair arranged and constructed to hold the release ring in the locked position.

20. An endovascular delivery device, for delivering an endograft, the endovascular delivery device comprising:
 a handle assembly at a distal end thereof;
 a nose assembly at a proximal end thereof,
 a guide wire catheter extending through the handle assembly, the guide wire catheter being affixed at a proximal end thereof to nose assembly;
 an endograft receiving portion extending distally with respect to the nose assembly;
 a pullable wire extending from the handle assembly to the endograft receiving portion; and
 a wire pull assembly, the assembly comprising:
  a rail assembly within the handle assembly defining an internal rail cavity and having a longitudinal axis; and
  a first hand-gripable slider assembly, the first hand-gripable slider assembly mounted to the rail assembly for relative sliding movement with respect to the rail assembly along the longitudinal axis, the first hand-gripable slider assembly comprising:
   a body slidably mounted to the rail assembly, the body having an inner body portion within the rail cavity, the inner body portion comprising a wire receiver disposed within the body and connected to the inner body portion and the pullable wire; and
   a release ring comprising a hand-gripable external annular surface extending 360 degrees around an outer body portion, the release ring mounted around the rail assembly and operably connected to the inner body portion, the release ring slideably moveable with respect to the inner body portion along the longitudinal axis from a locked position to an unlocked position,
  wherein, the first slider assembly is locked against sliding movement with respect to the rail assembly until the release ring is moved to the unlocked position and,
  wherein, in the unlocked position, the inner body portion is slideably moveable with the wire receiver by sliding movement of the release ring to pull the pullable wire.

* * * * *